United States Patent [19]
Gardner et al.

[11] Patent Number: 5,099,030
[45] Date of Patent: Mar. 24, 1992

[54] NOVEL COMPOUNDS, PHARMACEUTICAL COMPOSITIONS, AND METHODS FOR TREATING INFLAMMATION AND PAIN

[75] Inventors: Joseph H. Gardner, Cincinnati; Gerald B. Kasting, Wyoming; Thomas L. Cupps, Oxford; Richard S. Echler, Fairfield; Thomas W. Gibson, Cincinnati; Joel I. Shulman, Cincinnati, all of Ohio

[73] Assignee: The Procter & Gamble Company, Cincinnati, Ohio

[21] Appl. No.: 722,718

[22] Filed: Jun. 27, 1991

Related U.S. Application Data

[60] Division of Ser. No. 404,924, Sep. 8, 1989, Pat. No. 5,045,565, which is a continuation-in-part of Ser. No. 359,598, Jun. 1, 1989, abandoned, which is a continuation-in-part of Ser. No. 149,618, Feb. 12, 1988, abandoned, which is a continuation-in-part of Ser. No. 23,598, Mar. 9, 1987, abandoned.

[51] Int. Cl.$^5$ ............... C07D 207/00; C07C 125/00; C07C 103/30; C07C 103/38
[52] U.S. Cl. .................. 548/478; 514/487; 514/586; 514/595; 514/599; 514/603; 514/620; 558/234; 560/9; 560/29; 564/56; 564/85; 564/86; 564/162; 564/165; 564/27; 564/49; 564/51
[58] Field of Search ............ 514/487, 586, 595, 599, 514/603, 620; 558/234; 560/9, 29; 564/85, 86, 162, 165

[56] References Cited

U.S. PATENT DOCUMENTS

| | | | |
|---|---|---|---|
| 4,238,508 | 12/1980 | Nelson | 424/324 |
| 4,313,958 | 2/1982 | LaHann | 424/324 |
| 4,401,663 | 8/1983 | Buckwalter et al. | 424/321 |
| 4,424,205 | 1/1984 | LaHann et al. | 424/72 |
| 4,443,473 | 4/1984 | Buckwalter et al. | 424/300 |
| 4,460,602 | 7/1984 | Buckwalter et al. | 424/322 |
| 4,493,848 | 1/1985 | LaHann et al. | 424/324 |
| 4,532,139 | 7/1985 | Janusz et al. | 514/627 |
| 4,544,668 | 10/1985 | Janusz et al. | 514/563 |
| 4,544,669 | 10/1985 | LaHann et al. | 514/563 |
| 4,564,633 | 1/1986 | LaHann et al. | 514/538 |
| 5,045,565 | 9/1991 | Gardner et al. | 514/487 |

FOREIGN PATENT DOCUMENTS

| | | |
|---|---|---|
| 0187009 | 7/1986 | European Pat. Off. |
| 0206609 | 12/1986 | European Pat. Off. |
| 0282127 | 9/1988 | European Pat. Off. |
| WO89/04297 | 5/1989 | PCT Int'l Appl. |
| 2168975 | 7/1986 | United Kingdom |
| 2168976 | 7/1986 | United Kingdom |
| 2206347 | 1/1989 | United Kingdom |

OTHER PUBLICATIONS

Ferris, A. B., "New Approach to Insecticidal Paints", Aust. Commonwealth Dep. Supply Def. Stand. Lab., Tech. Note No. 89, 3 (1966) (Chem. Abs. 67: 22919a) (abstract only).

Hegyes, P. & S. Foldeak, "Synthesis of Homovanillic Acid Derivatives of Capsaicin-Like Effect", Acta. Phys. Chem., vol. 20 (1974), pp. 115-120.

Michalska, Z., L. Grodzinska & A. Zmuda, "Synthesis and Local Anesthetic Properties of N-Substituted 3,4-Dimethoxyphenethylamine Derivatives", Dept. Pharm. Pharmacol., vol. 24 (1972), pp. 17-25 (Chem. Abs. 77: 19271a) (abstract only).

Nelson, E. K., "Vanillyl-Acyl Amides", J. Am. Chem. Soc., vol. XLI (1919), pp. 2121-2130.

Primary Examiner—Asok Pal
Assistant Examiner—P. Achutamurthy
Attorney, Agent, or Firm—Milton B. Graff, IV; Kim William Zerby; Jerry J. Yetter

[57] ABSTRACT

The present invention relates to beta-aminoethyl-substituted phenyl compounds, especially beta-aminoethoxy-substituted phenyl compounds. The present invention also relates to pharmaceutical compositions comprising a safe and effective amount of a compound of the present invention and a pharmaceutically-acceptable carrier. The present invention further relates to methods for producing analgesia and reducing inflammation, in humans and lower animals, by administering the compounds or compositions of the present invention. In addition, the present invention relates to methods for making compounds of the present invention and intermediates useful in these synthesis methods.

23 Claims, No Drawings

NOVEL COMPOUNDS, PHARMACEUTICAL COMPOSITIONS, AND METHODS FOR TREATING INFLAMMATION AND PAIN

This is a division of application Ser. No. 404,924, filed on Sept. 8, 1989 now U.S. Pat. No. 5,045,565 issued, Sept. 2, 1991 which is a continuation-in-part of application Ser. No. 359,598 filed June 1, 1989, abandoned, which is a continuation-in-part of application Ser. No. 149,618 filed Feb. 12, 1988, abandoned, which is a continuation-in-part of application Ser. No. 023,598 filed Mar. 9, 1987, abandoned.

BACKGROUND OF THE INVENTION

The present invention relates to certain novel beta-amino ethyl-substituted phenyl compounds, especially beta-aminoethoxy-substituted phenyl compounds, which are effective as anti-inflammatory and/or analgesic agents. This invention also relates to methods for synthesizing compounds of the present invention, and intermediates useful in these synthesis methods. The present invention further relates to pharmaceutical compositions containing these compounds, which compositions are useful for treating diseases involving inflammation and/or pain. Finally, the present invention relates to methods for treating diseases characterized by inflammation or pain.

Inflammation, or the "inflammatory response", is the result of complex interconnected physiological events, including increased vascular permeability, fluid accumulations, and the migration of a changing population of inflammatory cells into the inflamed area. The clinical manifestations of inflammation include swelling (edema), increased local temperature, erythema, and pain. The inflammatory response can be triggered by any of a number of causative factors, including certain bacteria, radiation, hypersensitivity to chemical agents, arthritis-like conditions, and the like. The inflammatory response is generally believed to be a primary defense mechanism in the body, but, unchecked, can become excessive and can result in functional impairment.

The use of non-steroidal anti-inflammatory, antipyretic and analgesic drugs, especially the salicylates, which include aspirin and aspirin derivatives, to combat inflammation and attendant pain is accepted medical practice. The non-steroidals are commonly employed to relieve pain and inflammation associated with, for example, bursitis, arthritis, and the like.

While pain is incapable of precise definition due to its basically subjective nature, it can generally be said that the term refers to feelings of distress or suffering caused by stimulation of specialized nerve endings. A great variety of drugs have been developed to reduce pain in man and other animals; some directed to eliminating pain at its source, and others directed to blocking the assimilation of pain by the brain. Among the latter group of drugs that are designed to block the sensation of pain, are the analgesics, which generally relieve pain without causing unconsciousness. Analgesics can be further classified in two main categories: opioid analgesics, including morphine, codeine, levorphanol, and the morphine-like analgesics meperidine, and methadone; and antipyretic analgesics, such as aspirin, ibuprofen, phenacetin, acetaminophen, phenylbutazone, and indomethacin.

Although the precise pharmacological action of these analgesics is uncertain, there are certain effects which readily distinguish the opioid analgesics from the antipyretics. In particular, the antipyretics are weak analgesics, with much of their effect in the peripheral nervous system, so that behavioral changes do not usually occur. Generally, these analgesics relieve only somatic pain originating from muscles, joints, tendons and fasciae, and are ineffective against deep visceral pain. However, the opioid analgesics are quite effective against all types of pain, with broad-based action in the central nervous system. Aside from potent analgesia, the opioids, also known as narcotics, often produce effects on mood and other behavioral changes. Perhaps the most notable side effect of the opioid analgesics is the fact that their repeated use is associated with tolerance, as well as psychic and physical dependence.

It has been recently discovered that capsaicin, a natural product of certain species of the genus Capsicium, induces analgesia. Capsaicin (trans-8-methyl-N-vanillyl-6-nonenamide) and "synthetic" capsaicin (N-vanillyl-nonanamide) are disclosed as analgesics in U.S. Pat. No. 4,313,958, LaHann, issued Feb. 2, 1982. Analgesic activity of capsaicin has also been discussed in the chemical and medical literature, including Yaksh, et al, Science, 206. pp 481–483 (1979); Jancso, et al, Naunyn-Schmiedebero's Arch. Pharmacol., Vol. 311, pp 285–288 (1980) and Holzer et al, Eur. J. Pharm. Vol. 58, pp 511–514 (1979). U.S. Pat. No. 4,238,508, Nelson, issued Dec. 9, 1980, discloses 3-hydroxyacetanilide for use in producing analgesia in animals. European Patent Application 0089710, LaHann, et al, published Sept. 28, 1983, describes hydroxyphenylacetamides with analgesic and anti-irritant activity. Similarly, analgesic and anti-irritant activity is disclosed for N-vanillyl sulfonamides in U.S. Pat. No. 4,401,663, Buckwalter, et al, issued Aug. 30, 1983; hydroxyphenyl-acetamides in U.S. Pat. No. 4,424,205, LaHann, et al, issued Jan. 31, 1984; N-(3- or 4- hydroxy or 3,4-dihydroxybenzyl) carbamates in U.S. Pat. No. 4,443,473, Buckwalter, et al, issued Apr. 17, 1984; N-[(substituted phenyl) methyl]-cis-monounsaturated alkenamides in U.S. Pat. No. 4,493,848, LaHann, et al, issued Jan. 15, 1985; N-(3-methoxy-4-hydroxybenzyl and phenyl) ureas and thioureas in U.S. Pat. No. 4,460,602, Buckwalter, et al, issued July 17, 1984; N-vanillylureas in European Patent Application 0068590, Buckwalter, et al, published Jan. 5, 1983; N-[(substituted phenyl)methyl] alkynamides in U.S. Pat. No. 4,532,139, Janusz, et al, issued July 30, 1985; methylene substituted N-[(substituted phenyl)methyl] alkanamides in U.S. Pat. No. 4,544,668, Janusz, et al, issued Oct. 1, 1985; N-[(substituted phenyl) methyl]-diunsaturated amides in U.S. Pat. No. 4,544,669, LaHann, et al, issued Oct. 1, 1985; monoalkenamides in U.S. Pat. No. 4,564,633, LaHann, et al, issued Jan. 14, 1986; substituted phenylacetic acid esters in British Patent Specification 2,168,974, Loomans, et al, published July 2, 1986; N-(substituted alkyl)alkanamides and thioamides in British Patent Specification 2,168,976, Loomans, et al, published July 2, 1986; substituted aromatic-araalkanamides in British Patent Specification 2,168,975, Janusz et al, published July 2, 1986; combinations of capsaicinoids and arylalkanoic acids in European Patent Application Publication No. 149,545, Brand, published July 24, 1985; combinations of capsaicinoids and opioids in U.S. Pat. No. 4,599,342, LaHann, issued July 8, 1986; European Patent Application Publication No. 187,009, Janusz, et al., published July 9, 1986; European Patent Application Publication No. 206,609, Berman, et al., published Dec. 30, 1986; and beta-aminoethyl-substituted phenyl compounds in European Patent Application No. 282,127, Gardner, et al., published Sept. 14, 1988. The disclosures of all these patent specifications and articles are incorporated herein by reference in their entirety.

Notwithstanding the great effort already put forth to identify anti-inflammatory and analgesic agents, there remains a continuing need to identify new compounds and compositions which are effective for treating inflammation and/or pain. The compounds of the present invention are particularly useful for such purposes since systemic doses of these compounds can be administered to produce general analgesia and anti-inflammatory effects; or local doses can be administered to produce a local analgesic effect similar to that obtained with known local anesthetics. The opiate analgesics an. antipyretic analgesics which are presently widely used for general analgesia are typically not effective via local administration and thus are not generally used as local anesthetics. In addition, the compounds of the present invention are superior to known local anesthetics since they produce analgesia without the loss of mechanical sensation (i.e., "numbing") or motor coordination which are typically observed with the use of known local anesthetics. The properties of the compounds of the present invention therefore make these compounds uniquely suited for local administration before, during and/or after local surgical operations, such as oral surgeries and minor orthopedic surgeries.

An object of the present invention is therefore to provide compounds which can be administered to produce general analgesia and/or anti-inflammatory effects, or can be administered to produce local anesthesia without the associated negatives (e.g., numbness; loss of motor coordination) typically observed with known local anesthetics. Another object of the present invention is to provide compounds which are effective anti-inflammatory and/or analgesic agents, as well as pharmaceutical compositions containing these compounds. It is the further object of the present invention to provide methods for treating diseases characterized by inflammation or pain.

A still further object of the present invention is to provide compounds, and compositions containing these compounds, which have high efficacy, high potency, and/or good therapeutic indices. An additional object is to provide compounds and compositions which cause very little or no skin irritation when administered topically.

In addition, an object of the present invention is to provide compounds which are easily formulated and/or dosed. Another object is to provide compounds which are substantially water soluble. The present invention also relates to methods for synthesizing compounds of the present invention which give high yields and/or which are inexpensive; and to intermediates useful in these synthesis methods.

These and other objects will become readily apparent from the detailed description which follows.

All percentages and ratios used herein are by weight unless otherwise specified.

SUMMARY OF THE INVENTION

The present invention provides beta-aminoethyl-substituted phenyl compounds, and the pharmaceutically-acceptable salts and amides thereof, useful for relieving inflammation or producing analgesia in humans and lower animals, having the general structure:

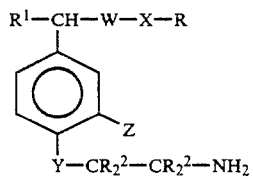

In this general structure, —W—X— moiety is selected from —C(O)NH—, —C(S)NH—, —S(O)$_2$NH—, —NHC(O)O—, —NHC(S))—, —NHC(O)NH—, and —NHC(S)NH— wherein either available bond of the —W—X— moiety is bonded to the —R moiety and the remaining bond is attached to the benzyl carbon atom (preferably —W—X— forms an amide or thioamide moiety); —Z is selected from hydrogen, hydroxy, and methoxy (preferred is methoxy); —R$^1$ is selected from hydrogen, hydroxy, alkyl esters of hydroxy having from about 1 to about 5 carbon atoms, alkyl having from about 1 to about 5 carbon atoms, and alkoxy having from about 1 to about 5 carbon atoms, (preferred are hydrogen, hydroxy, and methyl—most preferred is hydrogen); and each —R$^2$ is independently selected from hydrogen, halogen, unsubstituted or substituted alkyl having from about 1 to about 6 carbon atoms, substituted or unsubstituted aryl, and carboxylate, or two —R$^2$ moieties are covalently bonded to form a substituted or unsubstituted alkyl, heteroalkyl, aryl or heteroaryl ring having from about 3 to about 8 atoms in the ring including from 0 to about 3 heteroatoms. The —R group is a C$_1$-C$_{24}$ unsubstituted or substituted alkyl moiety which may be a straight, branched, or cyclic chain, and may also be saturated, monounsaturated, or polyunsaturated. Finally, the —Y— moiety is selected from —O—, —S— and —NR$^4$—, where R$^4$ is selected from hydrogen and C$_1$-C$_4$ alkanyl. Preferred are the beta-aminoethoxy-substituted phenyl compounds in which the —Y— moiety is oxygen.

This invention also provides pharmaceutical compositions comprising a safe and effective amount of the compounds of the present invention and a pharmaceutically-acceptable carrier. Also provided are methods for producing analgesia and reducing inflammation, in humans or lower animals, by administering the compounds or compositions of this invention.

The present invention further relates to methods for synthesizing the beta-aminoethoxy-substituted phenyl compounds of the present invention. One method comprises the steps of: (1) reacting a specific phenol compound with a specific vicinal dihalide (preferably a vicinal dibromide) to form a beta-haloethoxy phenyl compound; followed by (2) reacting the beta-haloethoxy phenyl compound with an azide salt (preferably sodium azide) to form a beta-azidoethoxy phenyl compound; followed by (3) reducing the azido moiety (preferably with SnCl$_2$) to form the betaaminoethoxy phenyl compound. The present invention also relates to the novel beta-haloethoxy phenyl compounds and novel betaazidoethoxy phenyl compounds which are useful intermediates in this synthesis method. Another synthesis method comprises the steps of (1) reacting a specific phenyl compound with a phthalimide salt (preferably a potassium phthalimide salt) to form a beta-phthalimidoethoxy phenyl compound; followed by (2) removing the phthalimido moiety with hydrazine to give the beta-aminoethoxy phenyl compound. The present invention also relates to the novel betaphthalimidoethoxy phenyl compounds which are useful intermediates in this synthesis method. Another synthesis method comprises the steps of (1) reacting a specific phenol compound (preferably as its phenolic anion) with a specific aziridine compound to form a nitrogen-substituted beta-aminoethoxy phenyl compound; followed by (2) reducing the nitrogen substituent off of the nitrogen-substituted beta-aminoethoxy phenyl compound (preferably with sodium metal in liquid ammonia) to form the beta-aminoethoxy phenyl compound.

DETAILED DESCRIPTION OF THE INVENTION

Analgesic and/or Anti-inflammatory Agents

The compounds useful in the present invention are betaaminoethyl-substituted phenyl compounds, and the pharmaceutically-acceptable salts and amides thereof, which are effective as anti-inflammatory and/or analgesic agents, having the general structure:

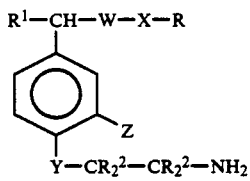

In this general structure, the —W—X— moiety is selected from —C(O)NH—, —C(S)NH—, —S(O)$_2$NH—, —NHC(O)O—, —NHC(S)O—, —NHC(O)NH— and —NHC(S)NH—. It is to be noted that either available bond of the —W—X— moiety may be bonded to the —R moiety, with the other bond being attached to the benzyl carbon atom.

It is preferred that for this general structure the —W— and —X— moieties are selected from —C(O)—, —C(S)— and —NH—, and —W—X— is an amide (i.e., —C(O)NH—) or thioamide (i.e., —C(S)NH—) moiety. Thus, the preferred —W—X— combination forms an amide or thioamide structure such that the compounds of the present invention are either phenylacetic acid amide or thioamide derivatives having the general structure:

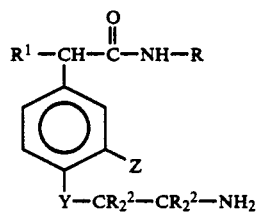

wherein =Q is oxygen or sulfur (preferred is =Q being oxygen); or vanillylamide or vanillylthioamide derivatives having the general structure:

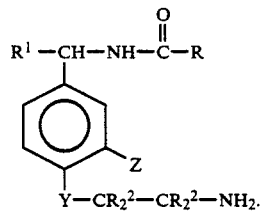

wherein =Q is oxygen or sulfur (preferred is =Q being oxygen).

The term "alkyl", as used herein, means carbon-containing chains which may be straight, branched, or cyclic; and which may be saturated, monounsaturated (i.e., one double or triple bond in the chain), or polyunsaturated (e.g., two double bonds in the chain; two triple bonds in the chain; one double and one triple bond in the chain). Alkyl groups may be substituted or, preferably, unsubstituted. Preferred substituents are selected from the group consisting of halogen, hydroxy, amino, aryl, carboxylate, and —OR$^3$ wherein —R$^3$ is an unsubstituted alkyl group having from about 1 to about 3 carbon atoms (especially methoxy and ethoxy). It is preferred that substituted alkyl groups be mono-, di- or tri-substituted, especially monosubstituted. The term "carboxylate", as used herein, means an organic carboxylic acid moiety (i.e., —CO$_2$H), and the salts (e.g., sodium, potassium, calcium, tetraethylammonium) and esters (e.g., methyl ester, ethyl ester) and amides (e.g., unsubstituted amide, N-methyl amide, N,N-dimethyl amide) thereof which are acceptable from a toxicity viewpoint for administration to humans or lower animals.

"aryl" and "heteroaryl", as used herein, mean aryl and heteroaryl rings which may be mono-, di-, tri-, or unsubstituted, preferably monosubstituted or unsubstituted, especially unsubstituted. Additionally, heteroaryl rings comprise at least one oxygen, sulfur or nitrogen atom in the ring structure. Preferred aryls and heteroaryls include unsubstituted or substituted phenyl, naphthyl, pyridyl, pyrimidyl, imidazolyl, furanyl, thiophenyl, pyrazolyl, triazolyl, tetrazolyl, thiazolyl, triazinyl, pyrrolyl, indolyl and purinyl; more preferred aryls and heteroaryls include phenyl, pyridyl, imidazolyl, furanyl and thiophenyl; most preferred aryl is substituted or unsubstituted phenyl. Preferred substituents include halogen, hydroxy, C$_1$-C$_{16}$ alkoxy, amino, nitro, cyano, phenyl, benzyl, benzyloxy, trifluoromethyl, formylamino, carboxylate, and C$_1$-C$_6$ alkyl. Preferred substituted aryl moieties are alkylaryls, preferably unsubstituted or substituted where the substituent groups are independently selected from halogen, hydroxy, amino, and carboxy groups; most preferred alkylaryl being a methylphenyl group.

As used herein, saturated alkyl groups are referred to as "alkanyl"; unsaturated alkyl groups comprising double bonds in the chain are referred to as "alkenyl" (preferred are chains having the double bonds in the "Z" geometric configuration); and unsaturated alkyl groups comprising triple bonds in the chain are referred to as "alkynyl". The designation of geometric configurations for any double bonds present in compounds of the present invention utilizes the art-known nomenclature "Z" and "E", and is fully described in Morrison and Boyd, Organic Chemistry. Third Edition (Allyn and Bacon, Inc., Boston; 1973), pp. 131-133 and 148-151; and March, *Advanced Organic Chemistry*, Second Edition (McGraw-Hill Book Company, New York; 1977), pp. 86-124; the disclosures of both these references being incorporated herein by reference in their entirety.

In the structures herein, the —$R^1$ moiety is selected from hydrogen, hydroxy, alkyl esters of hydroxy having from about 1 to about 5 carbon atoms, alkyl having from about 1 to about 5 carbon atoms, and alkoxy having from about 1 to about 5 carbon atoms, (especially hydrogen, hydroxy, and methyl), with preferred —$R^1$ being hydrogen. The —Z moiety is selected from hydrogen, hydroxy, and methoxy; with preferred —Z being selected from hydroxy and methoxy. Most preferred —Z is methoxy.

The —$R^2$ moieties are each independently selected from hydrogen, halogen, unsubstituted or substituted alkyl having from about 1 to about 5 carbon atoms, substituted or unsubstituted aryl, and carboxylate, or two —$R^2$ moieties are covalently bonded to form a substituted or unsubstituted alkyl, heteroalkyl, aryl or heteroaryl ring having from about 3 to about 8, preferably 3-6, atoms in the ring including from 0 to about 3 heteroatoms. It is preferred that no more than two —$R^2$'s are other than hydrogen. Preferred —$R^2$ substituents other than hydrogen include unsubstituted and substituted $C_1$-$C_6$ alkyl and unsubstituted and substituted phenyl.

It is preferred that at least one —$R^2$ on the alpha carbon atom (i.e., the carbon atom bonded directly to the —Y— moiety) be a hydrogen. Preferred also is all —$R^2$ being selected from hydrogen and hydroxyalkyl having from about 1 to about 5 carbon atoms (especially 5-hydroxypentyl, 2-hydroxybutyl or hydroxymethyl). Preferred also is all —$R^2$ being selected from hydrogen and aminoalkyl having from about 1 to about 5 carbon atoms (especially 5-aminopentyl, 2-aminobutyl, aminomethyl or aminoethyl). Preferred also is all —$R^2$ being selected from hydrogen and substituted or unsubstituted aryl (especially phenyl or methylphenyl). Also preferred is where one —$R^2$ on each of the alpha and beta carbon atoms is hydrogen and the other —$R^2$'s are bonded to form an aryl or heteroaryl ring, especially phenyl. Also preferred is where both —$R^2$ on the alpha carbon atom are hydrogen and at most only one —$R^2$ is other than hydrogen on the beta carbon atom (the carbon atom directly attached to the alpha carbon atom) and is selected from the group consisting of alkyl, hydroxyalkyl, aminoalkyl and substituted or unsubstituted aryls (especially hydroxymethyl, aminomethyl, aminoethyl, aminoethyl, phenyl and methylphenyl). Preferred also is all —$R^2$ being selected from hydrogen and alkyl having from about 1 to about 5 carbon atoms (especially methyl). More preferred is at most only one —$R^2$ being other than hydrogen, and most preferred is all —$R^2$ being hydrogen.

Particularly preferred is where both —$R^2$ on the alpha carbon atom are hydrogen and both —$R^2$ on the beta carbon atom are unsubstituted or substituted alkyl or are covalently bonded to form a substituted or unsubstituted alkyl or heteroalkyl ring having from about 3 to about 8 atoms, including from 0 to about 3 heteroatoms, in the ring. As used herein, "heteroatoms" means atoms other than carbon that can covalently bond to at least two other atoms and become part of a stable ring structure. Preferred heteroatoms are N, O and S. More preferred —$R^2$ on the beta carbon atom are unsubstituted or substituted $C_1$-$C_6$ alkyl, more preferably $C_1$-$C_4$ alkyl, more preferably still $C_1$-$C_2$ alkyl. Also preferred are the two —$R^2$ moieties on the beta carbon atom being covalently bonded to form a substituted or unsubstituted alkyl ring having from about 3 to about 6 carbon atoms, more preferably 3 or 4 carbon atoms in the ring. Preferred —$R^2$ alkyl moieties on the beta carbon atom are saturated or unsaturated having a single double or triple bond, more preferred is that both —$R^2$ on the beta carbon be unsubstituted or substituted alkanyl or covalently bonded to form an alkanyl ring. Preferred substituents of the —$R^2$ alkyl moieties on the beta carbon are hydroxy, amino, thiol and carboxylate, especially hydroxy and amino. More preferred is both —$R^2$ alkyl moieties on the beta carbon being unsubstituted. More preferred still is that both —$R^2$ on the beta carbon atom are methyl or ethyl, especially methyl.

The —Y— moiety is selected from —O—, —S— and —$NR^4$—, where $R^4$ is selected from hydrogen and $C_1$-$C_4$ alkanyl; preferably $R^4$ is hydrogen. Preferred —Y— is —O— which forms the beta-aminoethoxy-substituted phenyl compounds having the general structure:

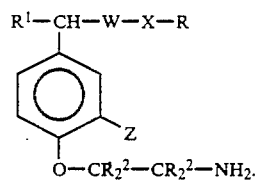

The —R group in the structures herein is an alkyl group having from about 1 to about 24 carbon atoms, preferably from about 6 to about 22 carbon atoms, and more preferably from about 14 to about 22 (especially from about 16 to about 20) carbon atoms for unsaturated alkyl groups and from about 6 to about 14 (especially from about 8 to about 12) carbon atoms for saturated alkyl groups.

Preferred —R groups are arylalkyl moieties where the alkyl portion has from 1 to about 12 carbon atoms, preferably from 1 to about 6 carbon atoms, more preferably 1 or 2 carbon atoms. The aryl portion of such —R group is preferably unsubstituted or substituted phenyl. Preferred substituents include halogen, nitro, cyano, phenyl, benzyl, benzyloxy, trifluoromethyl, formylamino, $C_1$-$C_{16}$ alkoxy and $C_1$-$C_4$ alkyl.

Preferred —R groups are straight and branched chain alkanyl, straight and branched chain monounsaturated alkyl, straight and branched chain diunsaturated alkyl, and straight and branched chain triunsaturated alkyl. More preferred —R groups are selected from straight and branched chain alkanyl, straight and branched chain alkenyl having one double bond, straight and branched chain alkenyl having two double bonds, and straight and branched chain alkenyl having three double bonds. Most preferred —R groups are selected from straight chain alkanyl and straight chain alkenyl having one double bond. Such preferred —R groups are preferably unsubstituted.

The preferred —R groups are as follows. For the compounds of the present invention which are phenylacetic acid amide or thioamide derivatives, particularly the beta-aminoethoxy-substituted compounds having the general structure:

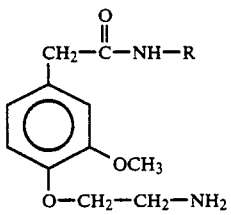

the preferred —R groups are selected from n-hexanyl, n-heptanyl, n-octanyl, n-nonanyl, n-decanyl, n-undecanyl, n-dodecanyl, n-tridecanyl, n-tetradecanyl, tetradecenyl, pentadecenyl, hexadecenyl, heptadecenyl, octadecenyl, nonadecenyl, eicosenyl, docosenyl, octadecadienyl, nonadecadienyl, eicosadienyl, octadecatrienyl, eicosatrienyl, eicosatetraenyl, octadecynyl, nonadecynyl, eicosynyl, and docosynyl. More preferred —R groups are selected from n-octanyl, n-nonanyl, n-decanyl, 9E- or 9Z-tetradecenyl, 9E- or 9Z-hexadecenyl, 9E- or 9Z-octadecenyl, 6E- or 6Z-octadecenyl, 11E- or 11Z-octadecenyl, 10E- or 10Z-nonadecenyl, 13E- or 13Z-docosenyl, 9-methylene-1-octadecanyl, 9Z, 12Z-octadecadienyl, 9E, 12E-octadecadienyl, 9Z, 12E-octadecadienyl, 9Z, 11E-octadecadienyl, 10E, 13E-nonadecadienyl, 11E, 14E-eicosadienyl, 9Z, 12Z, 15Z-octadecatrienyl, 6Z, 9Z, 12Z-octadecatrienyl, 11Z, 14Z, 17Z-eicosatrienyl, 5Z, 8Z, 11Z, 14Z-eicosatetraenyl, and 9-octadecynyl. Most preferred —R groups are n-octanyl, n-nonanyl, and 9Z-octadecenyl.

For the compounds of the present invention which are vanillylamide or vanillylthioamide derivatives, particularly the betaaminoethoxy-substituted compounds having the general structure:

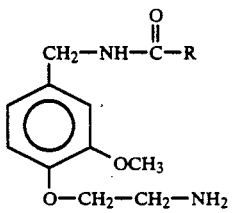

the preferred —R groups are selected from n-hexanyl, n-heptanyl, n-octanyl, n-nonanyl, n-decanyl, n-undecanyl, n-dodecanyl, n-tridecanyl, tridecenyl, tetradecenyl, pentadecenyl, hexadecenyl, heptadecenyl, octadecenyl, nonadecenyl, eicosenyl, docosenyl, heptadecadienyl, octadecadienyl, nonadecadienyl, eicosadienyl, heptadecatrienyl, octadecatrienyl, nonadecatrienyl, eicosatrienyl, nonadecatetraenyl, heptadecynyl, octadecynyl, nonadecynyl, and eicosynyl. More preferred —R groups are selected from n-heptanyl, n-octanyl, n-nonanyl, 8E- or 8Z-tridecenyl, 8E- or 8Z-pentadecenyl, 8E- or 8Z-heptadecenyl, 5E- or 5Z-heptadecenyl, 10E- or 10Z-heptadecenyl, 9E- or 9Z-octadecenyl, 12E- or 12Z-nonadecenyl, 8-methylene-1-heptadecanyl, 8Z, 11Z-heptadecadienyl, 8E, 11E-heptadecadienyl, 8Z, 11E-heptadecadienyl, 8Z, 10E-heptadecadienyl, 9E, 12E-octadecadienyl, 10E, 13E-nonadecadienyl, 8Z, 11Z, 14Z-heptadecatrienyl, 5Z, 8Z, 11Z-heptadecatrienyl, 10Z, 13Z, 16Z-nonadecatrienyl, 4Z, 7Z, 10Z, 13Z-nonadecatetraenyl, and 8-heptadecynyl. Most preferred —R groups are n-heptanyl, n-octanyl and 8Z-heptadecenyl (i.e., oleoyl amide).

The term "pharmaceutically-acceptable salts and amides", as used herein, means the compounds in their salt or amide form which have the same general pharmacological properties as the basic amino form from which they are derived, and which are acceptable from a toxicity viewpoint. Pharmaceutically-acceptable salts include ammonium salts derived from inorganic acids (e.g., HCl, HBr, NaHSO$_4$, H$_2$CO$_3$), and ammonium carboxylic acid salts derived from organic carboxylic acids (e.g., acetic acid; gluconic acid; citric acid; glucouronic acid; galactouronic acid; fumaric acid; gentisic acid; lactobionic acid; benzoic acid). Pharmaceutically-acceptable amides include those derived from organic carboxylic acids (e.g., acetic acid amides) including amino acids (e.g., glycine amides). Preferred are the ammonium carboxylic acid salts derived from organic carboxylic acids, especially the acetate and gluconate salts.

Compounds of the present invention include, for example, N-((4-(2-aminoethoxy)-3-methoxyphenyl)-methyl)-9Z-octadecenamide having the structure:

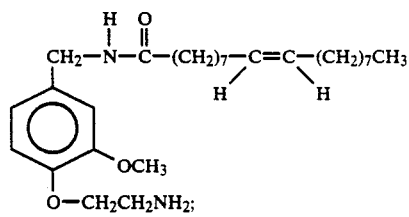

N-((4-(2-aminoethoxy)-3-methoxyphenyl)-methyl)-9Z-thiooctadecenamide having the structure:

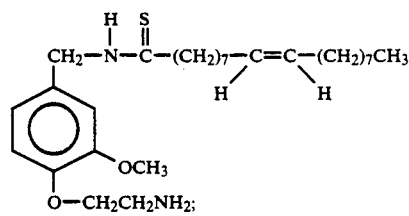

N-((4-(2-aminoethoxy)-3-methoxyphenyl)-methyl)-9Z-octadecenylsulfonamide having the structure:

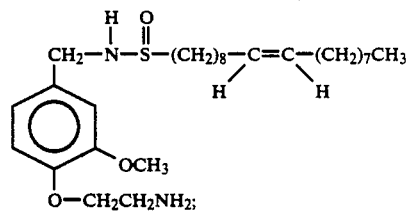

N-((4-(2-aminoethoxy)-3-methyl)-9Z-octadecenamide having the structure:

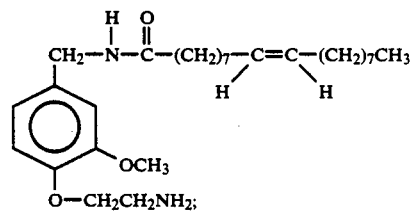

N-((4-(2-aminoethoxy)-phenyl)-methyl)-9Z-octadecenamide having the structure:

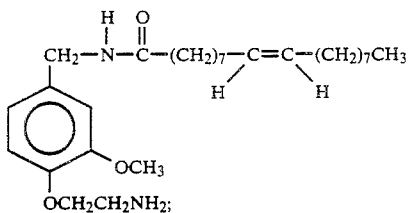

N-((4-(2-aminoethoxy)-3-methoxyphenyl)-methyl)-nonanamide having the structure:

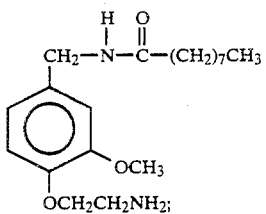

N-((4-(2-aminoethoxy)-3-methoxyphenyl)-methyl)-thiononanamide; ((4-(2-aminoethoxy)-3-methoxyphenyl)-methyl)-nonanylsulfonamide; N-((4-(2-aminoethoxy)-3-hydroxyphenyl)-methyl)-nonanamide; N-((4-(2-aminoethoxy)-phenyl)-methyl)-nonanamide; N-((4-(2-methyl-2-aminopropoxy)-3-methoxyphenyl)-methyl)-9Z-octadecenamide having the structure:

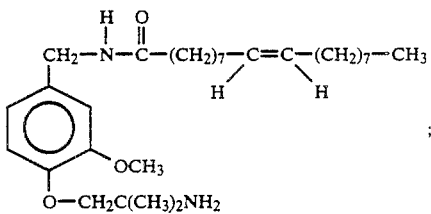

N-((4-(2-methyl-2-aminopropoxy)-3-methoxyphenyl)-methyl)-nonanamide; N-((4-(1-aminocyclopropanemethoxy)cyclopropanemethoxy)-3-methoxyphenyl)methyl)-9Z-octadecenamide having the structure:

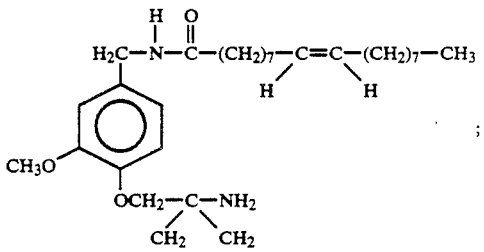

N-((4-(1-aminocyclopentanemethoxy)-3-methoxyphenyl)methyl-9Z-octadecenamide having the structure:

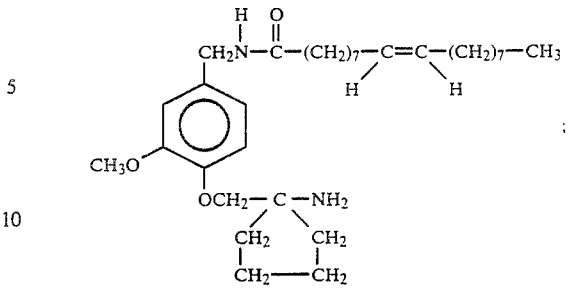

N-((4-(2(S)-amino-3-methylbutoxy)-3-methoxyphenyl)-methyl9Z-octadecenamide having the structure:

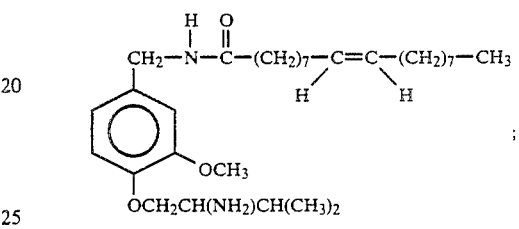

N-((4-(2-(carboxylic acid)-2-aminoethoxy)-3-methoxyphenyl)-methyl)-9Z-octadecenamide having the structure:

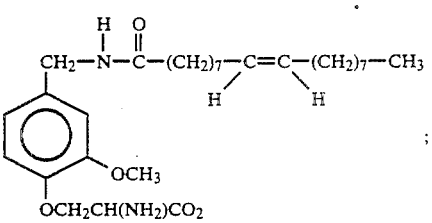

N-((4-(2-amino-3-hydroxypropoxy)-3-methoxyphenyl)-methyl)-9Z-octadecenamide having the structure:

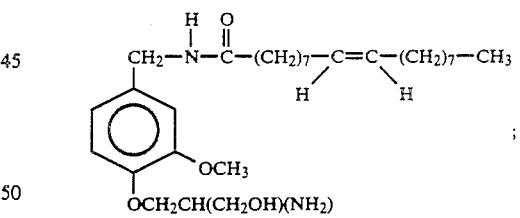

N-((4-(2-aminocyclopentoxy)-3-methoxyphenyl)-methyl)-9Z-octadecenamide; N-((4-(2-amino-3-hydroxypropoxy)-3-methoxyphenyl)-methyl)-nonanamide; N-((4-(2-amino-3-(carboxylic acid)-propoxy)-3methoxyphenyl)-methyl)-nonanamide; N-((4-(2-aminoethoxy)-3-methoxyphenyl)-methyl-octadecanamide; N-((4-(2-aminoethoxy)-3-methoxyphenyl)-methyl)-9-methylene-1-octadecanamide; N-((4-(2-aminoethoxy)-3-methoxyphenyl)-methyl)-11Z, 14Z, 17Z-eicosatrienamide; N-((4-(2-aminoethoxy)-3-methoxyphenyl)-methyl)-5Z, 8Z, 11Z, 14Z-eicosatetraenamide; N-((4-(2-aminoethoxy)-3-methoxyphenyl)methyl)-9-octadecynamide; N-((4-(2-aminoethoxy)-3-methoxyphenyl)methyl)-9Z-tetradecenylamide; N-((4-(2-aminoethoxy)3-methoxyphenyl)-methyl)-9Z-hexadecenamide; N-((4-(2-aminoethoxy)-3-methoxyphenyl)-methyl)-9E-octadecenamide;

N-((4-(2-aminoethoxy)-3-methoxyphenyl)-methyl)-13Z-docosenamide; N-((4-(2-aminoethoxy)-3-methoxyphenyl)-methyl)-hexanamide; N-((4-(2-aminoethoxy)-3-methoxyphenyl)-methyl)-octanamide; N-((4-(2-aminoethoxy)-3-methoxyphenyl)-methyl)-decanamide; N-((4-(2-aminoethoxy)-3-methoxyphenyl)-methyl)-tetradecanamide; N-((4-(2-aminoethoxy)-3-methoxyphenyl)-methyl)-9Z,12Z-octadecadienamide; N-((4-(2-aminoethoxy)-3-methoxyphenyl)-methyl)-9Z,12Z-thiooctadecadienamide; N-((4-(2-aminoethoxy)-3-methoxyphenyl)-methyl)dodecanamide; N-((4-(2-aminoethoxy)-3-methoxyphenyl)-methyl)hexadecanamide; N-(9Z-octadecenyl)-4-(2-aminoethoxy)-3-methoxyphenylacetamide having the structure:

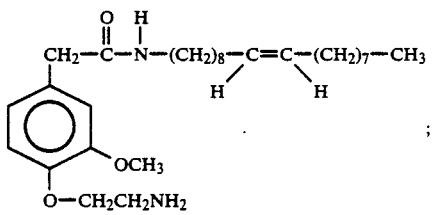

N-(9Z-octadecenyl)-4-(2-amino-2-methylpropoxy)-3-methoxyphenyl acetamide having the structure:

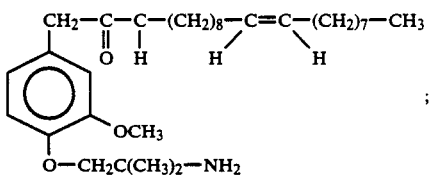

N-(9Z-octadecenyl)-4-(2-aminoethoxy)-3-methoxyphenylthioacetamide having the structure:

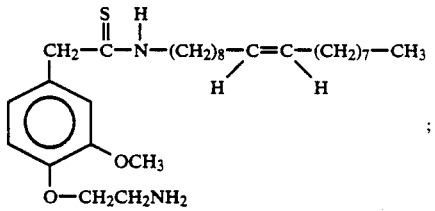

N-(9Z-octadecenyl)-4-(2-aminoethoxy)-3-methoxybenzylsulfonamide having the structure:

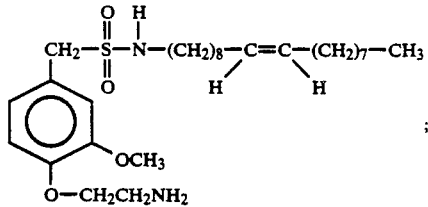

N-(9Z-octadecenyl)-4-(2-aminoethoxy)-3-hydroxyphenylacetamide; N-(9Z-octadecenyl)-4-(2-aminoethoxy)-phenylacetamide; N-octanyl-4-(2-aminoethoxy)-3-methoxyphenylacetamide; N-octanyl-4-(2-aminoethoxy)-3-methoxyphenylthioacetamide; N-octanyl-4-(2-aminoethoxy)-3-methoxybenzylsulfonamide; N-octanyl-4-(2-aminoethoxy)-3-hydroxyphenylacetamide; N-octanyl-4-(2-aminoethoxy)-phenylacetamide; N-(9Z-octadecenyl)-4-(2-methyl-2-aminopropoxy)-3-methoxyphenylacetamide; N-octadecanyl-4-(2-aminoethoxy)-3-methoxyphenylacetamide; N-(9-methylene-1-octadecanyl)-4-(2-aminoethoxy)-3-methoxyphenylacetamide; N-(11Z, 14Z, 17Z-eicosatrienyl)4-(2-aminoethoxy)-3-methoxyphenylacetamide; N-(5Z, 8Z, 11Z, 14Z-eicosatetraenyl)-4-(2-aminoethoxy)-3-methoxyphenylacetamide; N-(9-octadecynyl)-4-(2-aminoethoxy)-3-methoxyphenylacetamide; N-(9Z-tetradecenyl)-4-(2-aminoethoxy)-3-methoxyphenylacetamide; N-(9Z-hexadecenyl)-4-(2-aminoethoxy)-3-methoxyphenylacetamide; N-(9E-octadecenyl)-4-(2-aminoethoxy)-3-methoxyphenylacetamide; N-(13Z-docosenyl)-4-(2-aminoethoxy)-3-methoxyphenylacetamide; N-hexanyl-4-(2-aminoethoxy)-3-methoxyphenylacetamide; N-nonanyl-4-(2-aminoethoxy)-3-methoxyphenylacetamide; N-decanyl-4-(2-aminoethoxy)-3-methoxyphenylacetamide; N-tetradecanyl-4-(2-aminoethoxy)-3-methoxyphenylacetamide; N-(9Z, 12Z-octadecadienyl)-4-(2-aminoethoxy)-3-methoxyphenylacetamide; N-dodecanyl-4-(2-aminoethoxy)-3-methoxyphenylacetamide; (N-hexadecanyl-4-(2-aminoethoxy)-3-methoxyphenylacetamide; N-((4-(2-amino-2-carboxyethoxy)-3-methoxyphenyl)-methyl)-9Z-octadecenamide; N-((4-(2-aminoethylamino)3-methoxyphenyl)-methyl)-9Z-octadecenamide having the structure:

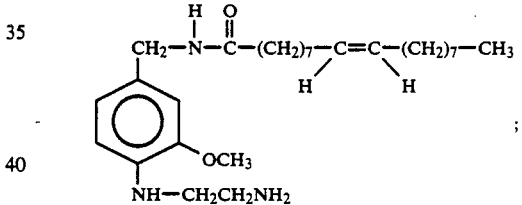

N-((4-(2-aminoethylamino)-3-methoxyphenyl)-methyl)-nonanamide; N-((4-(2-aminoethylamino)-3-methoxyphenyl)-methyl)octanamide; N-(9Z-octadecenyl)-4-(2-aminoethylamino)-3-methoxyphenylacetamide having the structure:

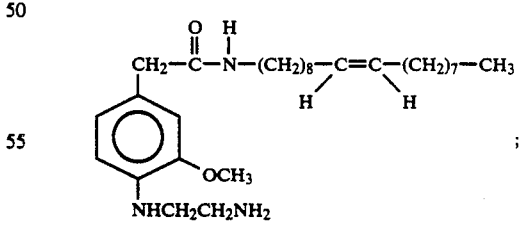

N-octanyl-4-(2-aminoethylamino)-3-methoxyphenylacetamide; N-((4-(2-aminoethylamino)-3-methoxyphenyl)-methyl)-9Z-thiooctadecenamide; N-((4-(2-aminoethylamino)-3-methoxyphenyl)methyl)-thiononanamide; N-(9Z-octadecenyl)-4-(2-aminoethylamino)-3-methoxyphenylthioamide; N-((4-mercapto-S-(2-aminoethyl)-3-methoxyphenyl)-methyl)-nonanamide having the structure:

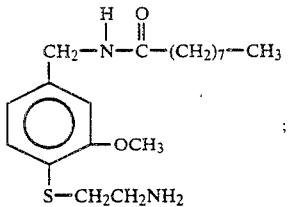

N-((4-mercapto-S-(2-aminoethyl)-3-methoxyphenyl)-methyl)-9Z-octadecenamide; N-((4-mercapto-S-(2-aminoethyl)-3-methoxyphenyl)methyl)-9Z-octanamide; N-(9Z-octadecenyl)-4-(mercapto-S-(2-aminoethyl))-3-methoxyphenylacetamide; N-octanyl-4-(mercapto-S-(2-aminoethyl))-3-methoxyphenylacetamide; N-((4-mercapto-S-(2-aminoethyl)-3-methoxyphenyl)-methyl)-9Z-thiooctadecenamide; N-((4-mercapto-S-(2-aminoethyl)-3-methoxyphenyl)-methyl)-thiononanamide; N-(9Z-octadecenyl)-4-(mercapto-S-(2-aminoethyl))-3-methoxyphenylthioacetamide; N-((4-(2-aminoethoxy)-3-methoxyphenyl)methyl)-9Z-octadecenylcarbamate having the structure:

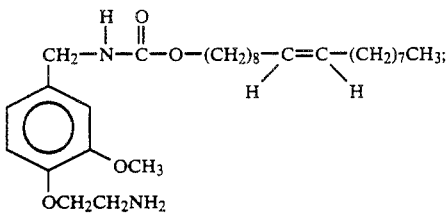

N-((4-(2-aminoethoxy)-3-methoxyphenyl)-methyl)-9Z-octadecenylthiocarbamate having the structure:

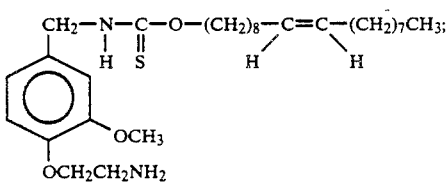

N-((4-(2-aminoethoxy)-3-methoxyphenyl)-methyl)-nonanylcarbamate; N-((4-(2-aminoethoxy)-3-methoxyphenyl)-methyl)-nonanylthiocarbamate; N-((4-(2-aminoethoxy)-3-methoxyphenyl)-methyl)octanylcarbamate; N-((4-(2-aminoethoxy)-3-methoxyphenyl)-methyl)-octanylthiocarbamate; N-(9Z-octadecenyl)-4-(2-aminoethoxy)-3-methoxybenzylcarbamate having the structure:

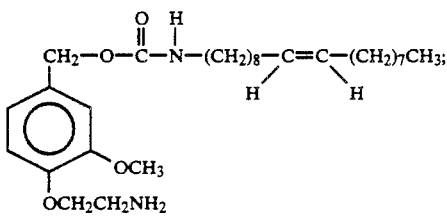

N-(9Z-octadecenyl)-4-(2-aminoethoxy)-3-methoxybenzylthiocarbamate; N-octanyl-4-(2-aminoethoxy)-3-methoxybenzylcarbamate; N-octanyl-4-(2-aminoethoxy)-3-methoxybenzylthiocarbamate; N-((4-(2-aminoethoxy)-3-methoxyphenyl)-methyl)-N'-(9Z-octadecenyl-)urea having the structure:

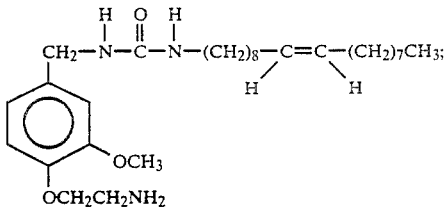

N-((4-(2-aminoethoxy)-3-methoxyphenyl)-methyl)-N'-(9Z-octadecenyl)thiourea having the structure:

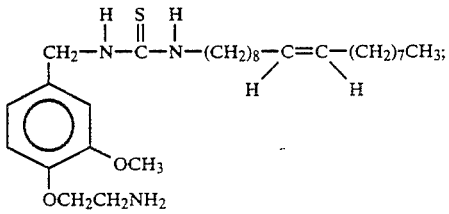

N-((4-(2-aminoethoxy)-3-methoxyphenyl)-methyl)-N'-nonanylurea; N-((4-(2-aminoethoxy)-3-methoxyphenyl)-methyl)-N'-nonanylthiourea; N-((4-(2-aminoethoxy)-3-methoxyphenyl)-methyl)-N'-octanylurea; N-((4-(2-aminoethoxy)-3-methoxyphenyl)-methyl)N'-octanylthiourea; and the pharmaceutically-acceptable salts and amides thereof.

Preferred compounds of the present invention are N-((4-(2-aminoethoxy)-3-methoxyphenyl)-methyl)-9Z-octadecenamide; N-((4-(2-aminoethoxy)-3-methoxyphenyl)-methyl)-nonanamide; N-((4-(2-methyl-2-aminopropoxy)-3-methoxyphenyl)-methyl)-9Z-octadecenamide; N-((4-(2(S)-amino-3-methylbutoxy)-3-methoxyphenyl)methyl)-9Z-octadecenamide; N-(9Z-octadecenyl)-4-(2-aminoethoxy)-3-methoxyphenylacetamide; N-octanyl-4-(2-aminoethoxy)-3-methoxyphenylacetamide; N-((4-(2-amino-3-hydroxypropoxy)-3-methoxyphenyl)-methyl)-9Z-octadecenamide; N-((4-(2-amino-2-carboxyethoxy)-3-methoxyphenyl)-methyl)-9Z-octadecenamide; N-((4-(2-methyl-2-aminopropoxy)-3-methoxyphenyl)-methyl)-nonanamide; N-((4-(2-methyl-2-aminopropoxy)-3-methoxyphenyl)-methyl)-9Z-octadecenamide; and the pharmaceutically-acceptable salts and amides thereof. Most preferred compounds of the present invention are N-((4-(2-aminoethoxy)-3-methoxyphenyl)-methyl)-9Z-octadecenamide; N-(9Z-octadecenyl)-4-(2-aminoethoxy)-3-methoxyphenylacetamide; N-((4-(2-aminoethoxy)-3-methoxyphenyl)-methyl)-nonanamide; N-(( 4-(2-methyl-2-aminopropoxy)-3-methoxyphenyl)-methyl)-nonanamide; N-((4-(2-methyl-2-aminopropoxy)-3-methoxyphenyl)-methyl)-9Z-octadecenamide; and the pharmaceutically-acceptable salts and amides thereof.

In order to determine and assess pharmacological activity, testing of these compounds in animals is carried out using various assays known to those skilled in the art. Thus, analgesic activity may be tested in art-known models such as the acetylcholine and phenylquinone models in mice, the Randall-Selitto model in rats, and the hot-plate test in mice or rats. The anti-inflammatory activity of the compounds can be conveniently demonstrated using an assay designed to test the ability of these compounds to antagonize the local edema which is characteristic of the inflammatory response. Examples of such known tests include the carrageenan rat edema test, the oxazolone-induced inflamed mouse ear test, and the arachidonic acid-induced inflamed mouse ear test. Another useful art-known test is the adjuvant arthritis test.

These and other appropriate tests for pharmacological activity are disclosed and/or referred to in U.S. Pat. No. 4,313,958, LaHann, issued Feb. 2, 1982; Yaksh, et al., *Science*, 206, pp. 481-483 (1979); Jancso, et al., *Naunyn-Schmiedeberg's Arch. Pharmacol.*, Vol. 311, pp. 285-288 (1980); Holzer et al., *Eur. J. Pharm.*, Vol., 58, pp. 511-514 (1979); U.S. Pat. No. 4,238,508, Nelson, issued Dec. 9, 1980; European Patent Application 089710, LaHann, et al., published Sept. 28, 1983; U.S. Pat. No. 4,401,663, Buckwalter, et al., issued Aug. 30, 1983; U.S. Pat. No. 4,424,205, LaHann, et al., issued Jan. 31, 1984; U.S. Pat. No. 4,443,473, Buckwalter, et al., issued Apr. 17, 1984; U.S. Pat. No. 4,493,848, LaHann, et al., issued Jan. 15, 1985; U.S. Pat. No. 4,460,602, Buckwalter, et al., issued July 17, 1984; European Patent Application 0068590, Buckwalter, et al., published Jan. 5, 1983; U.S. Pat. No. 4,532,139, Janusz, et al., issued July 30, 1985; U.S. Pat. No. 4,544,668, Janusz, et al., issued Oct. 1, 1985; U.S. Pat. No. 4,544,669, LaHann, et al., issued Oct. 1, 1985; U.S. Pat. No. 4,564,633, LaHann, et al., issued Jan. 14, 1986; British Patent Specification 2,168,974, Loomans, et al., published July 2, 1986; British Patent Specification 2,168,976, Loomans, et al., published July 2, 1986; British Patent Specification 2,168,975, Janusz, et al., published July 2, 1986; European Patent Application Publication No. 149,545, Brand, published July 24, 1985; U.S. Pat. No. 4,599,342, LaHann, issued July 8, 1986; European Patent Application Publication No. 187,009, Janusz, et al., published July 9, 1986; and European Patent Application Publication No. 206,609, Berman, et al., published Dec. 30, 11986; the disclosure of all these patent specifications and articles being incorporated herein by reference in their entirety. Certain of these tests for pharmacological activity are also described in more detail in the Examples provided hereinafter.

As noted hereinbefore, capsaicin and a wide variety of other substituted phenyl compounds are known to have analgesic and/or anti-inflammatory activity. Typically, however, these compounds are very difficult to formulate and dose due to insolubility in water. Attempts to improve water solubility for these types of compounds, for example by adding certain hydrophilic substituents to the phenyl ring, results in compounds which are not efficacious. Surprisingly, however, the beta-aminoethyl-substituted phenyl compounds of the present invention (which are chemically very similar to non-efficacious compounds having hydrophilic substituents) are substantially water soluble and are efficacious as analgesic and/or anti-inflammatory agents. In addition, relative to the previously disclosed capsaicinoid and phenylacetamide compounds which have demonstrated analgesic and/or anti-inflammatory activity, the compounds of the present invention are substantially more water soluble, are more efficacious and/or more potent particularly when administered orally, and are generally less irritating to skin.

The compounds of the present invention are prepared from readily-available materials. Techniques useful for the preparation of the present compounds, and starting materials for the preparation of the present compounds, are described in U.S. Pat. No. 4,313,958, LaHann, issued Feb. 2, 1982; U.S. Pat. No. 4,238,508, Nelson, issued Dec. 9, 1980; European Patent Application 0089710, LaHann, et al., published Sept. 28, 1983; U.S. Pat. No. 4,401,663, Buckwalter, et al., issued Aug. 30, 1983; U.S. Pat. No. 4,424,205, LaHann, et al., issued Jan. 31, 1984; U.S. Pat. No. 4,443,473, Buckwalter, et al., issued Apr. 17, 1984; U.S. Pat. No. 4,493,848, LaHann, et al., issued Jan. 15, 1985; U.S. Pat. No. 4,460,602, Buckwalter, et al., issued July 17, 1984; European Patent Application 0068590, Buckwalter, et al., published Jan. 5, 1983; U.S. Pat. No. 4,532,139, Janusz, et al., issued July 30, 1985; U.S. Pat. No. 4,544,668, Janusz, et al., issued Oct. 1, 1985; U.S. Pat. No. 4,544,669, LaHann, et al., issued Oct. 1, 1985; U.S. Pat. No. 4,564,633, LaHann, et al., issued Jan. 14, 1986; British Patent Specification 2,168,974, Loomans, et al., published July 2, 1986; British Patent Specification 2,168,976, Loomans, et al., published July 2, 1986; British Patent Specification 2,168,975, Janusz, et al., published July 2, 1986; European Patent Application Publication No. 149,545, Brand, published July 24, 1985; U.S. Pat. No. 4,599,342, LaHann, issued July 8, 1986; European Patent Application Publication No. 187,009, Janusz, et al., published July 9, 1986; and European Patent Application Publication No. 206,609, Berman, et al., published Dec. 30, 1986; the disclosure of all these patent specifications being incorporated herein by reference in their entirety. Representative procedures for synthesizing compounds of the present invention are provided hereinafter.

The compounds of the present invention typically comprise from about 0.00001% to about 99.9% by weight of the pharmaceutical compositions of the present invention, preferably from about 0.0001% to about 50%, and most preferably from about 0.0001% to about 25%.

Pharmaceutically-acceptable Carrier

In addition to the pharmaceutical agent as described hereinbefore, the pharmaceutical compositions of the present invention essentially comprise a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical compositions are capable of being commingled with the compound of the present invention, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such a peanut oil, cottonseed oil, sesame oil, olive oil, corn oil and oil of theobroma; polyols such as propylene glycol, glycerine, sorbitol, mannitol, and polyethylene glycol; sugar; alginic acid; pyrogen-free water; isotonic saline; phosphate buffer solutions; cocoa butter (suppository base); emulsifiers, such as the Tweens ®; as well as other non-toxic compatible substances used in pharmaceutical formulations. Wetting agents and lubricants such as sodium lauryl sulfate, as well as coloring agents, flavoring agents, excipients, tableting agents, stabilizers, antioxidants, and preservatives, can also be present. Other compatible pharmaceutical additives and actives (e.g., NSAI drugs; pain killers; muscle relaxants) may be included in the pharmaceutically-acceptable carrier for use in the compositions of the present invention. For example, art-known local anesthetics may be included in the pharmaceutically-acceptable carrier (e.g., benzyl alcohol; Novocaine ®; lidocaine).

The choice of a pharmaceutically-acceptable carrier to be used in conjunction with the compounds of the present invention is basically determined by the way the compound is to be administered. The preferred modes of administering the compounds of the present invention are by injection, orally and topically. If the compound is to be injected, the preferred pharmaceutically-acceptable carrier is sterile, physiological saline, the pH of which has been adjusted to about 4. Suitable pharmaceutically-acceptable carriers for topical application include those suited for use in creams, gels, tapes and the like; and for oral administration include those suited for tablets and capsules.

The pharmaceutically-acceptable carrier employed in conjunction with the compounds of the present invention is used at a concentration sufficient to provide a practical size to dosage relationship. The pharmaceutically-acceptable carriers, in total, may comprise from about 0.1% to about 99.99999% by weight of the pharmaceutical compositions of the present invention, preferably from about 50% to about 99.9999%, and most preferably from about 75% to about 99.9999%.

Total single dosages of the compounds of the present invention present in pharmaceutical compositions herein are generally from about 1 ug to about 10 g. Preferred single dosages are from about 1 ug to about 3500 mg; more preferred are from about 1 ug to about 1000 mg; and most preferred are from about 1 ug to about 600 mg.

Specific oral, topical, and injectable formulations useful in this invention are described in the following U.S. Patents, all incorporated by reference herein: U.S. Pat. No. 4,401,663, Buckwalter, et al, issued Aug. 30, 1983; U.S. Pat. No. 4,424,205, LaHann, et al, issued Jan. 31, 1984; U.S. Pat. No. 4,443,473, Buckwalter, et al, issued Apr. 12, 1984; U.S. Pat. No. 4,493,848, LaHann, et al, issued Jan. 15, 1984. Representative pharmaceutical compositions of the present invention are provided in the Examples hereinafter.

Pharmaceutically-acceptable carriers suitable for the preparation of unit dosage forms for oral administration and injection, and dosage forms for topical application are well-known in the art. Their selection will depend on secondary considerations like taste, cost, and/or shelf stability, which are not critical for the purposes of the present invention, and can be made without difficulty by a person skilled in the art. Pharmaceutically acceptable carriers useful in the compositions of the present invention are described more fully hereinafter.

A. Oral Dose Forms

Various oral dosage forms can be used, including such solid forms as tablets, capsules, granules, bulk powders and microcapsules of the drug. These oral forms comprise a safe and effective amount, usually at least about 5%, and preferably from about 25% to about 50% of the compound of the present invention. Tablets can be compressed, enteric-coated, sugar-coated or film-coated containing suitable binders, lubricants, surfactants, diluents, disintegrating agents, coloring agents, flavoring agents, preservatives, flow-inducing agents, and melting agents. Liquid oral dosage forms include aqueous and nonaqueous solutions, emulsions, suspensions, solutions and/or suspensions reconstituted from non-effervescent granules, containing suitable solvents, preservatives, emulsifying agents, suspending agents, diluents, sweeteners, melting agents, coloring agents, and flavoring agents. Preferred carriers for oral administration include gelatin and propylene glycol. Specific examples of pharmaceutically acceptable carriers and excipients that may be used in formulating oral dosage forms containing compounds of the present invention are described in U.S. Pat. No. 3,903,297, Robert, issued Sept. 2, 11975, incorporated by reference herein. Techniques and compositions for making solid oral dosage forms are described in Marshall, "Solid Oral Dosage Forms," *Modern Pharmaceutics, Vol. 7*. (Banker and Rhodes, editors), 359–427 (1979), incorporated herein by reference. Techniques and compositions for making tablets (compressed, formulas and molded), capsules (hard and soft gelatin) and pills are described in *Remington's Pharmaceutical Sciences* (Arthur Osol, editor), 1553–1593 (1980), incorporated herein by reference.

The preferred unit dosage form for oral administration is tablets, capsules and the like, comprising a safe and effective amount of a compound of the present invention. Preferably oral dose forms comprise from about 10 mg to about 3500 mg of a compound of the present invention, more preferably from about 25 mg to about 1000 mg, and most preferably from about 50 mg to about 600 mg.

B. Topical Dose Forms

The compositions of the present invention can also be administered topically to a biological subject, i.e., by the direct laying on or spreading of the composition on epidermal or epithelial tissue. Such compositions include lotions, creams, solutions, gels and solids. These topical compositions comprise a safe and effective amount, usually from about 0.1% to about 10%, and preferably from about 1% to about 5%, of the compound of the present invention. Suitable carriers for topical administration of these compounds preferably remain in place on the skin as a continuous film and resist being washed off easily by perspiration or by immersion in water. Generally, the carrier is either organic in nature or an aqueous emulsion and capable of having the analgesic and/or anti-inflammatory agent dispersed or dissolved therein. The carrier may include pharmaceutically-acceptable emollients, skin penetration enhancers, coloring agents, fragrances, emulsifiers, thickening agents, and solvents. A more detailed description of such forms follows:

1. Lotions

The lotions can comprise an effective amount (preferably from about 0.1% to about 10%) of the compound of the present invention; from 1% to 25%, preferably from 3% to 15%, of an emollient; the balance being water, a $C_2$ or $C_3$ alcohol, or a mixture of water and the alcohol. Several emollients are known. Examples of such emollients are as follows:

a. Hydrocarbon oils and waxes. Examples are mineral oil, petrolatum, paraffin, ceresin, ozokerite, microcrystalline wax, polyethylene, and perhydrosqualene.

b. Silicone oils, such as dimethylpolysiloxanes, methylphenylpolysiloxanes, water-soluble and alcohol-soluble silconeglycol copolymers.

c. Triglyceride fats and oils such as those derived from vegetable, animal and marine sources. Examples include castor oil, safflower oil, cotton seed oil, corn oil, olive oil, cod liver oil, almond oil, avocado oil, palm oil, sesame oil, and soybean oil.

d. Acetoglyceride esters, such as acetylated monoglycerides.

e. Ethoxylated glycerides, such as ethoxylated glyceryl monostearate.

f. Alkyl esters of fatty acids having 10 to 20 carbon atoms. Methyl, isopropyl and butyl esters of fatty acids are useful herein. Examples include hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

g. Alkenyl esters of fatty acids having 10 to 20 carbon atoms. Examples thereof include oleyl myristate, oleyl stearate, and oleyl oleate.

h. Fatty acids having 9 to 22 carbon atoms. Suitable examples include pelargonic, lauric, myristic, palmitic, stearic, isostearic, hydroxystearic, oleic, linoleic, ricinoleic, arachidonic, behenic, and erucic acids.

i. Fatty alcohols having 10 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.

j. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.

k. Ether-esters such as fatty acid esters of ethoxylated fatty alcohols.

l. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

m. Polyhydric alcohols and polyether derivatives. Propylene glycol, dipropylene glycol, polypropylene glycol (M.W. 2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200–6000), methoxy polyethylene glycols 350, 550,750, 2000, 5000, poly[ethylene oxide] homopolymers (M.W. 100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol) $C_{15}$–$C_{18}$ vicinal glycol, and polyoxypropylene derivates of trimethylolpropane are examples thereof.

n. Polyhydric alcohol esters. Ethylene glycol mono- and di-fatty acid esters, diethylene glycol mono- and di-fatty acid esters, polyethylene glycol (M.W. 200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

o. Wax esters such as beeswax, spermaceti, myristyl myristate, stearyl stearate.

p. Beeswax derivatives, e.g., polyoxyethylene sorbitol beeswax. These are reaction products of beeswax with ethoxylated sorbitol of varying ethylene oxide content, forming a mixture of ether-esters.

q. Vegetable waxes including carnauba and candelilla waxes.

r. Phospholipids such as lecithin and derivatives.

s. Sterols. Cholesterol, cholesterol fatty acid esters are examples thereof.

t. Amides such as fatty acid amides, ethoxylated fatty acid amides, solid fatty acid alkanolamides.

The lotions further comprise from 1% to 10%, preferably from 2% to 5%, of an emulsifier. The emulsifiers can be nonionic, anionic or cationic. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, an alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound of the present invention is dissolved in the mixture. Conventional optional components can be included. One such additive is a thickening agent at a level from 1% to 10% of the composition. Examples of suitable thickening agents include: cross-linked carboxypolymethylene polymers, ethyl cellulose, polyethylene glycols, gum tragacanth, gum kharaya, xanthan gums and bentonite.

2. Creams

Compositions of this invention also can be formulated in a cream form. The creams comprise an effective amount (preferably from about 0.1% to about 10%) of the compound of the present invention; from 5% to 50%, preferably from 10% to 25%, of an emollient; the balance being water. The emollients above described can also be used in the cream compositions. Optionally the cream form contains a suitable emulsifier, as previously described. When an emulsifier is included, it is in the composition at a level from 3% to 50%, preferably from 5% to 20%.

3. Solutions

The compositions of this invention can be also formulated in a solution form. The solution form comprises an effective amount (preferably from about 0.1% to about 10%) of the compound of the present invention; the balance being water and/or a suitable organic solvent. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, ethanol, isopropanol, diethyl tartrate, butanediol, and mixtures thereof. Such solvent systems can also contain water.

These compositions in the solution form can be applied to the skin as is, or else can be formulated into an aerosol and applied to the skin as a spray-on. The aerosol compositions further comprise from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used at a level sufficient to expel the contents of the container.

4. Gels

Compositions herein can be formulated into a gel form by simply admixing a suitable thickening agent to the previously described solution compositions. Examples of suitable thickening agents have been previously described with respect to the lotions.

The gelled compositions comprise an effective amount (preferably from about 0.1% to about 10%) of the compound of the present invention; from 5% to 75%, preferably from 10% to 50%, of an organic solvent as previously described; from 0.5% to 20%, preferably from 1% to 10% of the thickening agent; the balance being water.

5. Solids

The compositions of this invention can also be formulated into a solid form. Such forms have use as a stick-type composition intended for application to the lips or other part of the body. Such compositions comprise an effective amount (preferably from about 0.1% to about 10%) of the compound of the present invention and from 50% to 98%, preferably from 60% to 90%, of the previously described emollients. This composition can further comprise from 1% to 20%, preferably from 5% to 15%, of a suitable thickening agent, and optionally emulsifiers and water. Thickening agents previously described with respect to lotions are suitable herein.

Additives commonly found in topical compositions such as preservatives, e.g., methyl and ethyl-paraben, dyes and perfume can be included in any of the previously described topical compositions.

The preferred dosage form for topical administration is a lotion comprising a safe and effective amount of the analgesic agent of the present invention, which is preferably a concentration of from about 0.01 mg/ml to about 10 mg/ml, more preferably from about 0.1 mg/ml to about 5 mg/ml, and most preferably from about 0.5 mg/ml to about 2 mg/ml. While topical application is preferably utilized to produce localized analgesic effects, systemic effects can also be achieved by utilizing larger dosages of the topical compositions and/or greater surface area coverage.

C. Injectable Dose Forms

The compounds of the present invention are also useful when injected. The dosage of the compound of the present invention which is both safe and effective to provide analgesic or antiirritant activity will vary with the particular condition being treated, the severity of the condition, the duration of treatment, the specific compound employed and its usage concentration, and like factors within the specific knowledge and expertise of the attending physician and commensurate with a reasonable benefit/risk ratio associated with the use of any drug compound. In addition, lower dosages will be utilized when only local analgesia is desired, whereas higher dosages will be utilized when general analgesia is desired. The injectable dosages and dosage ranges given herein are based on delivery of the compound of the present invention to a 70 kg human and can be adjusted to provide equivalent dosages for patients of different body weights.

Methods and materials for manufacturing injectables can be found in *Remington's Pharmaceutical Sciences*, 17ed., 1985, Chapter 85, p. 1518, the disclosures of which are incorporated herein by reference in their entirety. Materials for use in injectables are also described more fully hereinafter.

Generally, three types of injectable dosage forms are preferred: 1) aqueous solutions; 2) non-aqueous solutions; and 3) emulsions. The above dosage forms typically contain from about 0.001 mg/ml to about 10 mg/ml, preferably from about 0.1 mg/ml to about 1 mg/ml, more preferably from about 0.4 mg/ml to about 0.6 mg/ml.

The aqueous solutions preferably consist of water (preferably from about 80% to about 90%), a suitable solubilizer, various types of acids, and an antimicrobial agent. Several solubilizers are known. Examples of such solubilizers are as follows: urea compounds (e.g., urea; urethan); surfactants (e.g., Tweens; Spans; sodium deoxycholate and Pluronics); cellulosic agents (e.g., carboxymethylcellulose); carbohydrates (e.g., sorbitol; mannitol); B vitamins (e.g., nicotinamide); xanthine derivatives; and alcohols (e.g., benzyl alcohol). Examples of acids to be used include the following: glucuronic; galacturonic; fumaric; gentisic; acetic; citric and lactobionic. Types of antimicrobial agents that can be used are the following: phenylmercuric nitrate; thimerosal; benzethonium chloride; benzalkonium chloride; phenol; cresol; and chlorobutanol. An art-known local anesthetic (e.g., benzyl alcohol; Novocaine®; lidocaine) may also be included.

Non-aqueous solutions can comprise solvents which are either miscible with water or immiscible with water. Non-aqueous solvents miscible with water are mixed with water to yield a concentration preferably between from about 5% to about 90%. Examples of typical non-aqueous solvents miscible with water include: solvents used at 100% (e.g., propylene glycol; polyethylene glycol; dimethylformamide; dimethylacetamide); solvents mixed with water to yield a concentration of between from about 5% to about 90% (e.g., ethanol; glycerin; butylene glycol; tetraglycol; dimethylacetamide; dimethylformamide; lactic acid; ethyl acetate; N-B-hydroxyethyl lactamide; tetraethylurea; acetone; sulfolane; isopropylene glycol ether; hexenyl glycol; diethylene glycol dimethyl ether; tetrahydrofurfuryl methyl ether; N,N-dimethylmethoxyacetamide).

Non-aqueous solvents not miscible with water are primarily vegetable oils. Some common lipid solvents not miscible with water for injectable compositions are sesame oil, olive oil, arachis oil, maize oil, almond oil, cottonseed oil, castor oil, ethyl oleate, ethyl carbonate and isopropyl myristate.

Emulsions can be of either the water-in-oil (W/O) or the oil-in-water (OW) type. Typical oils are listed hereinbefore. The continuous phase is preferably about 99% of the formulation while the discontinuous phase is preferably about 1% of the formulation. Emulsifiers and stabilizers are typically used to complete the formulation. Examples of typical emulsifying agents are: surface active agents (e.g., sodium deoxycholate; Span; Tween); and natural surface active agents (e.g., Sorbit; phosphatidylcholine).

Injectable dose forms for producing general analgesia typically comprise from about 0.1 mg to about 1000 mg, and preferably from about 0.5 of to about 700 mg, of the compound of the present invention. Injectable dose forms for producing local analgesia typically comprise from about 1 ug to about 500 ug of the compound of the present invention.

Methods for Producing Anti-Inflammatory Activity and Analgesia

The present invention also encompasses methods of producing anti-inflammatory activity and/or analgesia (either general analgesia or local analgesia) in humans or lower animals through administering, to the human or lower animal in need of such treatment, a safe and effective amount of a compound of the present invention. This amount can be given in a single dose or multiple doses repeatedly over the course of the treatment. While dosages higher than those described hereinbefore are effective to reduce inflammation and produce analgesia, care must be taken in some individuals to prevent adverse side effects. The compounds and compositions of this invention can be used to treat and prevent pain, to provide analgesia, and/or to reduce inflammation in various disorders at the deeper structures, muscles, tendons, bursa and joints associated with disease and trauma, and in various other conditions in which non-steroidal anti-inflammatory, antipyretic and analgesic drugs, such as aspirin, and opioids, such as morphine, have heretofore been used to alleviate pain and discomfort and reduce inflammation.

The preferred modes of administration are orally, topically, and by injection, including, e.g., dermatomucosally (for example, dermally, rectally and the like) and parenterally (for example, by subcutaneous injection, intramuscular injection, intra-articular injection, intravenous injection and the like). Ocular administration and inhalation is also included. Thus, specific modes of administration include, without limitation, oral, transdermal, mucosal, sublingual, intramuscular, intravenous, intraperitoneal, and subcutaneous administration, as well as topical application.

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific analgesic agent employed, the particular pharmaceutically-acceptable carrier utilized, whether general or local analgesia is desired, and like factors within the knowledge and expertise of the attending physician. However, daily dosages can range from about 0.1 mg/kg of body weight to about 500 mg/kg of body weight. Preferred daily dosages are from about 1 to about 100 mg/kg of body weight. Up to about 6 single dosages per day may be administered.

Topical administration can be used to reduce inflammation and produce local or systemic analgesia, through directly laying on or spreading a safe and effective amount of the compound or composition of the present invention on epidermal or epithelial tissue, including outer skin and oral, gingival, and nasal tissue. The amount of the pharmaceutical composition to be topically administered may vary from about 0.01 mg/cm$^2$ to 5 mg/cm$^2$, and if a patch is worn over the affected area possibly higher concentrations, depending upon such factors as the sensitivity, type and location of tissue to be treated, the composition and carrier (if any) to be administered, and the particular compound to be administered as well as the particular disorder to be treated and the extent to which systemic (as distinguished from local) effects are desired. The extent of systemic analgesia also depends upon such factors as the amount of compound, the area of tissue to be covered, and the ability of the compound to penetrate the skin tissue.

Oral administration can be used to reduce inflammation and produce analgesia through oral dosing of a pharmaceutical composition comprised of a safe and effective amount of the compound of the present invention in a suitable oral pharmaceutical carrier. The compound is absorbed by the gastrointestinal tract. The pharmaceutical composition may consist of solid dosage forms such as tablets, hard gelatin capsules, soft gelatin capsules, bulk powders, and microcapsules of the drug. Alternately, it may consist of a liquid dosage form such as an aqueous or nonaqueous solution, emulsion, or suspension.

The amount of the compound ingested depends upon the bioavailability of the compound from the oral pharmaceutical composition. Typically, however, the compounds of the present invention are dosed in an amount of from about 0.1 mg/kg of body weight to about 500 mg/kg, and preferably from about 1 to about 100 mg/kg of body weight. The amount of the pharmaceutical composition depends upon the percent of compound within its formula, which is a function of the amount of the compound required per dose, its stability, release characteristics and other pharmaceutical parameters. Generally, the oral pharmaceutical composition should comprise from about 5% to about 50% of the compound of the present invention.

The preferred method of injectable administration is via a sterile aqueous solution of pH from about 3 to about 8 (more preferred is pH of from about 3 to about 6) or as a sterile emulsion. Larger amounts of drug can be administered to produce systemic analgesia using doses in the range of 0.01 to 10.0 mg/kg; however, smaller amounts of the drug can be administered via injection to produce a local analgesic and/or anti-inflammatory effect. The smaller quantities of drug to be administered are typically in the range of from about 1 to about 500 ug/injection; these amounts are used to produce a local analgesic effect without the numbing affect commonly associated with a local anesthetic. Such low doses avoid any significant systemic exposure to the drug and thereby greatly reduce the possibility of side effects. These local administrations may be useful for the treatment of pain and inflammation associated with minor surgical procedures, e.g., minor oral surgeries, tooth extractions, etc., or minor orthopedic surgeries. The preferred modes of administration for producing local analgesia are interdermally, subcutaneously, percutaneously, and intramuscularly.

Systemic administration can also be used to reduce inflammation and produce general analgesia. Such administration may be intravenously, intramuscularly, or subcutaneously. The amount of pharmaceutical composition typically administered may vary from about 0.5 to about 5 ml of a solution or suspension of the compound of the present invention in a pharmaceutically-acceptable carrier in a single dose. These compositions may also be administered systemically in multiple dosages, or by infusion.

Methods for Synthesizing Compounds of the Present Invention

The present invention also encompasses methods for synthesizing the analgesic and/or anti-inflammatory agents of the present invention. These novel methods are useful for synthesizing these compounds in high yield and/or at low cost.

a) Azide Reduction Synthesis Method

This novel method for preparing beta-aminoethoxy-substituted phenyl compounds of the present invention provides a low cost and high yield route to obtaining these compounds. This method comprises the steps of:

(1) reacting, to form a beta-haloethoxy phenyl compound:

(a) a phenol compound having the structure:

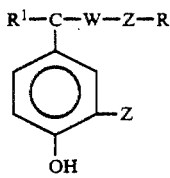

wherein: the —W—X— moiety is selected from the group consisting of —C(O)NH—, —C(S)NH—, —S(O)$_2$NH—, —NHC(O)O—, —NHC(S)O—, —NHC(O)NH— and —NHC(S)NH— wherein either available bond of the —W—X— moiety is bonded to the —R moiety and the remaining bond is attached to the benzyl carbon atom; —Z is selected from the group consisting of hydrogen, hydroxy, and methoxy; —R is an alkyl group having from about 6 to about 24 carbon atoms; —R$^1$ is selected from the group consisting of hydrogen, hydroxy, alkyl esters of hydroxy having from about 1 to about 5 carbon atoms, alkyl having from 1 about to about 5 carbon atoms, and alkoxy having from about 1 to about 5 carbon atoms; and (b) a vicinal dihalide having the structure:

$$X-CR^2_2CR^2_2-X$$

wherein: X is halogen; and each —R$^2$ is independently selected from hydrogen, halogen, unsubstituted or substituted alkyl having from about 1 to about 5 carbon atoms, substituted or unsubstituted aryl, and carboxylate, or two —R$^2$ moieties are covalently bonded to form a substituted or unsubstituted alkyl ring having from about 3 to about 7 carbon atoms in the ring; followed by (2) reacting the beta-haloethoxy phenyl compound with an azide salt (e.g., sodium azide; potassium azide) to form a beta-azidoethoxy phenyl compound; followed by (3) reducing the azido moiety to an amino moiety to form the beta-aminoethoxy phenyl compound.

Preferably, this method comprises the steps of (1) reacting the phenol compound with a vicinal dibromide having the structure Br—CR$^2_2$CR$^2_2$—Br to form a beta-bromoethoxy phenyl compound; followed by (2) reacting the beta-bromoethoxy phenyl compound with an azide salt to form a beta-azidoethoxy phenyl compound; followed by (3) reducing the azido moiety to an amino moiety with SnCl$_2$ to form the beta-aminoethoxy phenyl compound.

This preferred azide reduction method of the present invention generally involves the following reaction scheme:

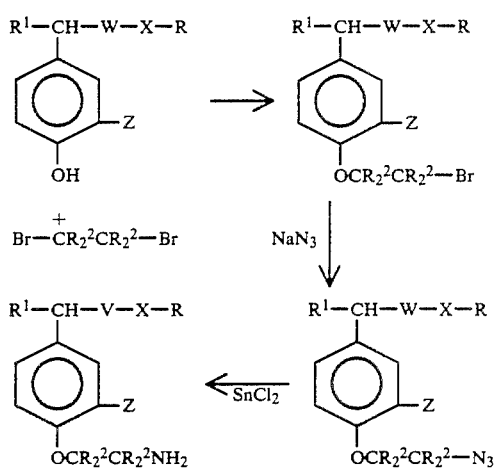

The phenol starting materials for this synthesis method are known compounds disclosed, for example, in the references incorporated hereinbefore by reference. The vicinal dihalides, particularly vicinal dibromides (e.g., 1,2-dibromoethane), are known compounds which are either commercially available or readily synthesized by art-known methods such as are disclosed, for example, in Morrison and Boyd, *Organic Chemistry*. Third Edition (Allyn and Bacon, Inc., Boston; 1973) pp. 186–187 and pp. 197–199, the disclosures of which are incorporated herein by reference in their entirety. The use of this method to synthesize compounds of the present invention is described more fully in the Examples hereinafter.

The present invention further relates to the novel beta-haloethoxy phenyl compounds and beta-azidoethoxy phenyl compounds which are useful intermediates in this synthesis method. These substituted phenyl compounds have the general structure:

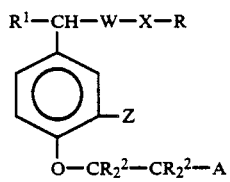

wherein: the —W—X— moiety is selected from the group consisting of —C(O)NH—, —C(S)NH—, —S(O)$_2$NH—, —NHC(O)O—, —NHC(S)O—, —NHC(O)NH— and —NHC(S)NH— wherein either available bond of the —W—X— moiety is bonded to the —R moiety and the remaining bond is attached to the benzyl carbon atom; —A is selected from the group consisting of halogen and —N$_3$; —Z is selected from the group consisting of hydrogen, hydroxy, and methoxy; —R$^1$ is an alkyl group having from about 6 to about 24 carbon atoms; —R is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and each —R$^2$ is independently selected from hydrogen, halogen, unsubstituted or substituted alkyl having from about 1 to about 5 carbon atoms, substituted or unsubstituted aryl, and carboxylate, or two —R$^2$ moieties are covalently bonded to form a substituted or unsubstituted alkyl ring having from about 3 to about 7 carbon atoms in the ring. The preferred W, X, —Z, —R, —R$^1$, and —R$^2$ groups are as described hereinbefore for the beta-aminoethoxy phenyl compounds. Most preferred is —R being hydrogen, —Z being methoxy, —W—X— being —C(O)NH—, and —A being bromine or —N$_3$. Representative compounds are described in the Examples hereinafter.

b) Phthalimide Synthesis Method

This novel method for preparing beta-aminoethoxy-substituted phenyl compounds of the present invention provides a low cost and high yield route to obtaining these compounds. This method comprises the steps of:

(1) reacting, to form a beta-haloethoxy phenyl compound:

(a) a phenol compound having the structure:

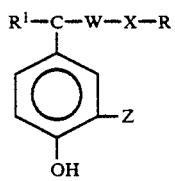

wherein: the —W—X— moiety is selected from the group consisting of —C(O)NH—, —C(S)NH—, —S(O)$_2$NH—, —NHC(O)O—, —NHC(S)O—, —NHC(O)NH— and —NHC(S)NH— wherein either available bond of the —W—X— moiety is bonded to the —R moiety and the remaining bond is attached to the benzyl carbon atom; —Z is selected from the group consisting of hydrogen, hydroxy, and methoxy; —R is an alkyl group having from about 6 to about 24 carbon atoms; —R$^1$ is selected from the group consisting of hydrogen, hydroxy, alkyl esters of hydroxy having from about 1 to about 5 carbon atoms, and alkoxy having from about 1 to about 5 carbon atoms; and (b) a vicinal dihalide having the structure:

$$X—CR_2^2CR_2^2—X$$

wherein: X is halogen; and each —R$^2$ is independently selected from hydrogen, halogen, unsubstituted or substituted alkyl having from about 1 to about 5 carbon atoms, substituted or unsubstituted aryl, and carboxylate, or two —R$^2$ moieties are covalently bonded to form a substituted or unsubstituted alkyl ring having from about 3 to about 7 carbon atoms in the ring; followed by (2) reacting the beta-haloethoxy phenyl compound with a phthalimide salt (e.g. potassium phthalimide) to form a beta-phthalimidoethoxy phenyl compound; followed by (3) reacting the beta-phthalimidoethoxy phenyl compound with hydrazine to remove the phthalimido group and form the beta-aminoethoxy phenyl compound.

Preferably, this method comprises the steps of (1) reacting the phenol compound with a vicinal dibromide having the structure Br—CR$_2^2$CR$_2^2$—Br to form a beta-bromoethoxy phenyl compound; followed by (2) reacting the beta-bromoethoxy phenyl compound with an phthalimide salt to form a beta-phthalimidoethoxy phenyl compound; followed by (3) reacting the beta-phthalimidoethoxy compound with NH$_2$NH$_2$ to form the beta-aminoethoxy phenyl compound. This preferred phthalimide synthesis method of the present invention-generally involves the following reaction scheme:

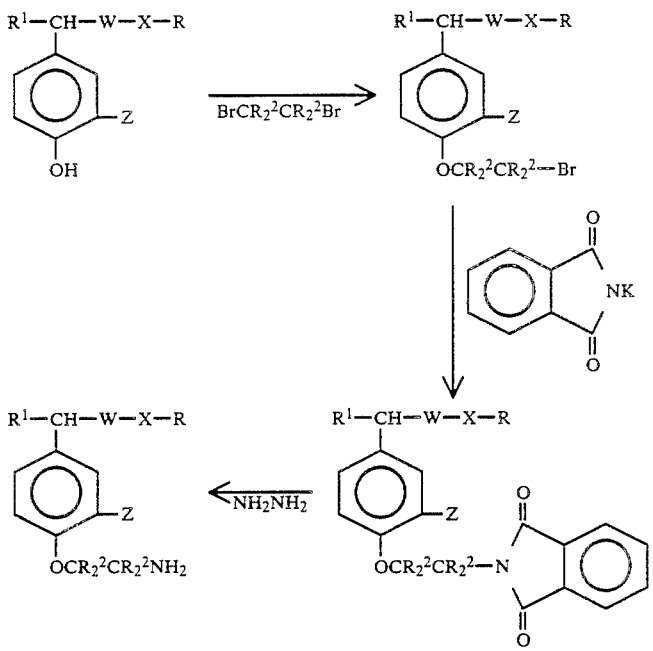

The phenol starting materials for this synthesis method are known compounds disclosed, for example, in the references incorporated hereinbefore by reference. The vicinal dihalides, particularly vicinal dibromides (e.g., 1,2-dibromoethane), are known compounds which are either commercially available or readily synthesized by art-known methods such as are disclosed, for example, in Morrison and Boyd, *Organic Chemistry*, Third Edition (Allyn and Bacon, Inc., Boston; 1973) pp. 186-187 and pp. 197-199, the disclosures of which are incorporated herein by reference in their entirety. The use of this method to synthesize compounds of the present invention is described more fully in the Examples hereinafter.

The present invention further relates to the novel beta-phthalimidoethoxy phenyl compounds which are useful intermediates in this synthesis method. These substituted phenyl compounds have the general structure:

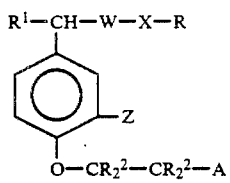

wherein: the —W—X— moiety is selected from the group consisting of —C(O)NH—, —C(S)NH—, —S-(O)$_2$NH—, —NHC(O)O—, —NHC(S)O—, —NH-C(O)NH— and —NHC(S)NH— wherein either available bond of the —W—X— moiety is bonded to the —R moiety and the remaining bond is attached to the benzyl carbon atom; —A is selected from the group consisting of halogen and phthalimide; —Z is selected from the group consisting of hydrogen, hydroxy, and methoxy; —R is an alkyl group having from about 6 to about 24 carbon atoms; —R$^1$ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and each —R$^2$ independently selected from hydrogen, halogen, unsubstituted or substituted alkyl having from about 1 to about 5 carbon atoms, substituted or unsubstituted aryl, and carboxylate, or two —R$^2$ moieties are covalently bonded to form a substituted or unsubstituted alkyl ring having from about 3 to about 7 carbon atoms in the ring. The preferred W, X, —Z, —R, —R$^1$, and —R$^2$ groups are as described hereinbefore for the beta-aminoethoxy phenyl compounds. Most preferred is —R$^1$ being hydrogen, —Z being methoxy, —W—X— being —C(O)NH—, and —A being bromine or phthalimide. Representative compounds are described in the Examples hereinafter.

c) Aziridine Synthesis Method

This novel method for preparing beta-aminoethoxy-substituted phenyl compounds of the present invention provides a high yield route to obtaining these compounds. The method comprises the steps of:

(1) reacting, to form a nitrogen-substituted beta-aminoethoxy phenyl compound:

(a) a phenol compound having the structure:

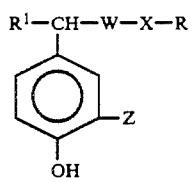

wherein: the —W—X— moiety is selected from the group consisting of —C(O)NH—, —C(S)NH—, —S-(O)$_2$NH—, —NHC(O)O—, —NHC(S)O—, —NH-C(O)NH— and —NHC(S)NH— wherein either available bond of the —W—X— moiety is bonded to the —R moiety and the remaining bond is attached to the benzyl carbon atom; —Z is selected from the group consisting of hydrogen, hydroxy, and methoxy; —R is an alkyl group having from about 6 to about 24 carbon atoms; and —$R^1$ is selected from the group consisting of hydrogen, hydroxy, alkyl esters of hydroxy having from about 1 to about 5 carbon atoms, alkyl having from about to about 5 carbon atoms, and alkoxy having from about 1 to about 5 carbon atoms;

(b) an aziridine compound having the structure:

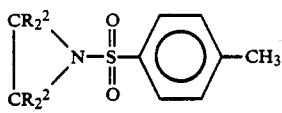

wherein each —$R^2$ is independently selected from hydrogen, halogen, unsubstituted or substituted alkyl having from about 1 to about 5 carbon atoms, substituted or unsubstituted aryl, and carboxylate, or two —$R^2$ moieties are covalently bonded to form a substituted or unsubstituted alkyl ring having from about 3 to about 7 carbon atoms in the ring; followed by (2) reducing the nitrogen substituent off of the nitrogen-substituted beta-aminoethoxy phenyl compound to form the beta-aminoethoxy phenyl compound.

Preferably, this method comprises the steps of: (1) reacting the phenol compound as its phenolic anion with the aziridine compound; followed by (2) reducing the nitrogen substituent off of the nitrogen-substituted beta-aminoethoxy phenyl compound with sodium metal in liquid ammonia.

This preferred aziridine synthesis method of the present invention generally involves the following reaction scheme:

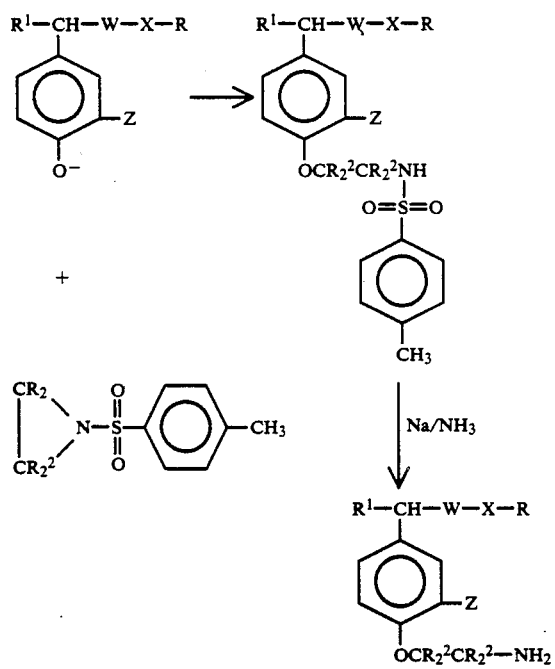

The phenol compounds which are the starting materials for the aziridine synthesis method are readily synthesized by artknown methods as described hereinbefore. The aziridine compounds are readily synthesized by art-known methods, for example, as described in March, *Advanced Organic Chemistry.* 3rd Edition (J. Wiley & Sons, New York; 1985), p. 325; and are readily converted to the N-(para-toluenesulfonyl)-aziridine compound by simple reaction of the aziridine with para-toluenesulfonyl chloride. The use of this method to synthesize representative compounds of the present invention is described more fully in the Examples hereinafter.

The following Examples further describe and demonstrate the preferred embodiments within the scope of the present invention. The Examples are given solely for the purpose of illustration, and are not to be construed as limitations of the present invention since many variations thereof are possible without departing from its spirit and scope. All temperature readings are in °C.

EXAMPLE I

Synthesis of
N-((4-(2-aminoethoxy)-3-methoxyphenyl)-methyl-nonanamide

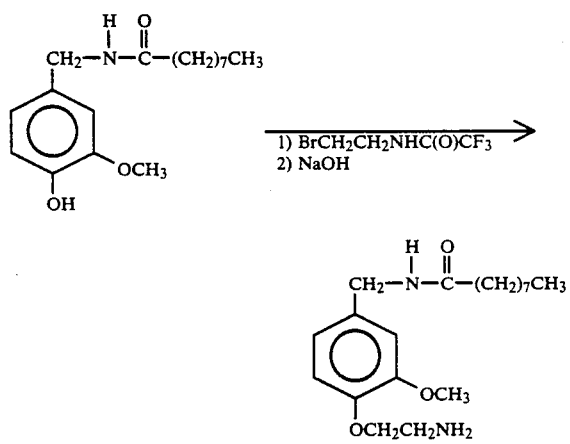

To a flame dried 5L, 3 neck, round bottom flask is added N-vanillylnonanamide (20.9 g; 71.3 millimole; which is disclosed in U.S. Pat. No. 4,313,958, to La-Hann, issued Feb. 2, 1982, incorporated by reference in its entirety herein), hexamethylphosphoramide (49.65 mL) and 2830 mL of dimethylformamide. After dissolving at room temperature with mechanical stirring, potassium tert-butoxide (28 g; 249.7 millimole) is added with stirring. A solution containing (N-trifluoroacetyl)-2-bromo-aminoethane (17.3 g; 78.5 millimole) in 170 mL of dimethylformamide is added dropwise over a period of 1 hour to the mixture described above with continuous stirring. The reaction mixture is then heated to 80° C. in an oil bath for 18 hours, after which time it is allowed to cool to room temperature. The reaction mixture is then concentrated to a volume of approximately 200 mL under vacuum. The concentrated residue is diluted to 6 L with diethyl ether and washed successively with 2×4 L of 0.5N HCl, 2×4 L of water, and 500 mL of saturated sodium chloride. The ether layer is dried over magnesium sulfate and evaporated to a white solid. The white solid product is recrystallized from ether to yield 10.07 g of the desired product N-((4-(2-(N'-trifluoroacetyl)-aminoethoxy)3-methoxy-phenyl)-methyl)-nonanamide (yield 32%).

The N-((4-(2-(N'-trifluoroacetyl)-aminoethoxy)-3-methoxyphenyl)-methyl)-nonanamide (10.07 g) is dissolved in 400 mL of ethanol, and 23.2 mL of 2.5 N sodium hydroxide is added. The reaction is stirred at room temperature for 2 hours and then diluted with 2 L of water. The aqueous mixture is extracted with ethyl acetate (4×500 mL), and the ethyl acetate extracts are combined, washed with saturated sodium chloride, and dried over anhydrous sodium sulfate. The ethyl acetate solution is concentrated to yield 7.7 g of solid product which is purified as follows.

The crude product is dissolved in 70 mL of warm chloroform and loaded onto a silica gel column. The column is eluted under reduced presure (aspirator) with 2700 mL of chloroform and the eluant is discarded. The column is then eluted with 1500 mL of a solvent mixture containing chloroform 93%, triethylamine 2%, and methanol 5%. This second eluant is collected, concentrated, and then dried to yield 6.86 g of white solid product N-((4-(2-aminoethoxy)-3-methoxyphenyl)-methyl)-nonanamide (yield 88%). m.p. =118°-119° C.; $^1$H-NMR (CDCl$_3$): 0.97 (3H, t), 1.2–2.0 (14H, m), 2.25 (2H, t), 3.17 (2H, t), 3.9 (3H, s), 4.15 (2H, t), 4.45 (2H, d), 6.0 (1H, m), 6.85 (3H, br s, aromatic).

Starting with the compound N-oleyl-4-hydroxy-3-methoxyphenylacetamide (which is disclosed in European Patent Application Publication No. 206,609, Berman et al., published Dec. 30, 1986, the disclosures of which are incorporated herein by reference in their entirety) and using substantially the same method as described hereinbefore, the compound N-(9Z-octadecenyl)-4-(2-aminoethoxy)-3-methoxyphenylacetamide is prepared. $^1$H NMR (CDCl$_3$): 0.9 (3H, t), 1.25 (br s, 24H), 1.75 (s, 2H), 1.8–2.1 (m, 4H), 3.0–3.25 (m, 4H), 3.5 (s, 2H), 3.85 (s, 3H), 4.05 (t, 2H), 5.2–5.6 (m, 3H), 6.9 ppm (br s, 3H).

EXAMPLE II

Synthesis of
N-((4-(2-aminoethoxy)-3-methoxyphenyl)-methyl)-9Z-octadecenamide by the Azide Reduction Method times with water and the aqueous washings are then combined and extracted once with CHCl$_3$ (250 ml). The organic phases are combined, washed with 10% H$_3$PO$_4$ (250 ml), saturated NaHCO$_3$ (250 ml), brine, then dried (MgSO$_4$) and filtered. The volume is reduced to less than 500 ml by vacuum distillation and the liquid is then transferred to a 4-L flask. After cooling to approximately 10° C., Et$_2$O (2 L) is added and the flask is cooled in an ice bath. A white precipitate forms and additional Et$_2$O is added to make a volume of 4 . The thick amorphous solid is filtered, washed with Et$_2$O, dried and used without further purification Mp=96°-97° C. $^1$H NMR (CDCl$_3$) (ppm): 6.8 (s, 3H), 5.9 (m, 1H), 5.3 (t, 2H J=5 Hz), 4.3 (m, 4H), 3.8 (s, 3H), 3.6 (t, 2H, J=6.5 Hz), 2.3–2.1 (m, 4H), 2.0–1.5 (m, 2H), 1.2 (s, 22H), 0.85 (t, 3H). $^{13}$C NMR (CDCl$_3$) (ppm): 14.0, 22.5, 25.6, 27.0, 29.1, 31.7, 36.5, 43.0, 55.8, 69.3, 111.9, 115.0, 119.8, 129.5, 132.8, 146.5, 149.8, 172.8.

(b) Synthesis of N-((4-(2-azidoethoxy)-3-methoxyphenyl)-methyl)-9Z-octadecenamide:

N-((4-(2-bromoethoxy)-3-methoxyphenyl)-methyl)-9Z-octadecenamide (182.0 gm, 0.347 mole), sodium azide (100 gm, 1.54 mole), tetrabutylammonium hydrogen sulfate (12.0 gm, 0.035 mole) and benzene (600 ml) are combined in a 2 L flask equipped with a thermometer, mechanical stirrer and reflux condenser. The solution is heated to a gentle reflux for 24 hours. The solution is transferred to a 6 L separatory funnel using 2 L of EtAc to wash the inorganic residue. The solution is then extracted with water (2 L), 10% H$_3$PO$_4$ (1 L), saturated NaHCO$_3$ (1 L), dried (MgSO$_4$) and concentrated to give 156 gm (92%) of a white solid. Purification is accomplished using a Waters prep 500 HPLC (two columns) eluting with CHCl$_3$ to give 146 gm (86%) of pure azide. Mp=71°–73° C. $^1$H NMR (CDCl$_3$)

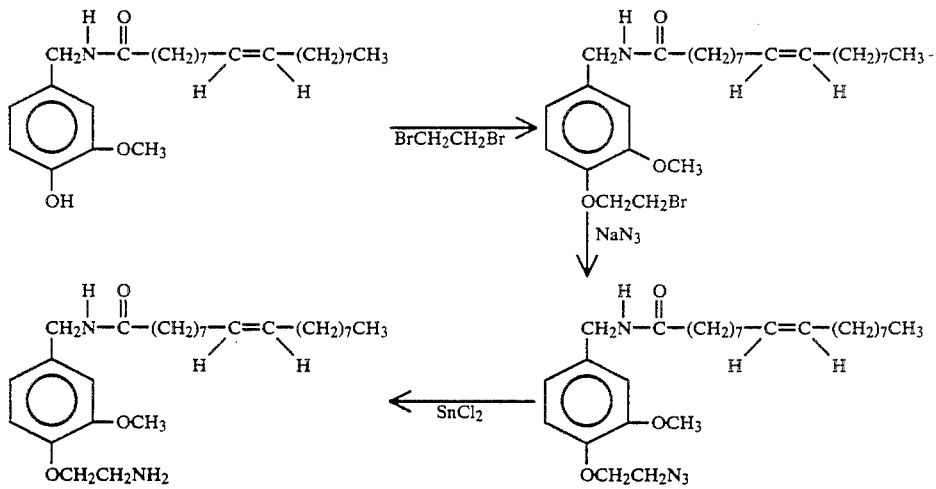

(a) Synthesis of N-((4-(2-bromoethoxy)-3-methoxyphenyl)methyl)-9Z-octadecenamide:

(N-vanillyloleamide (100 gm, 0.24 mole; which is prepared as described in U.S. Pat. No. 4,493,848 to LaHann and Buckwalter, issued Jan. 15, 1985), 1,2-dibromoethane (500 ml), 40% KOH (165 ml) and 40% tetrabutylammonium hydroxide (15 ml) are combined in a 2 L flask equipped with a thermometer, mechanical stirrer and reflux condenser, and the solution is heated to 55° C. The disappearance of starting material is monitored by TLC (6% acetone/CH$_2$Cl$_2$). After the reaction is completed (typically after reacting overnight), the solution is diluted with CHCl$_3$ (500 ml), washed three (ppm): 6.8 (s, 3H), 6.1 (m, 1H), 5.3 (t, 2H, J=4.5), 4.3 (d, 2H, J=5.5), 4.1 (t, 2H, J=5), 3.8 (s, 3H), 3.5 (t, 2H, J=5), 2.2–1.5 (m, 4H), 1.4 (m, 2H), 1.3 (s, 22H), 0.84 (t, 3H). $^{13}$C NMR (CDCl$_3$) (ppm): 172.9, 150.0, 147.0, 132.7, 129.6, 119.8, 114.6, 111.9, 68.3, 55.8, 50.1, 43.1, 36.6, 31.8, 29.1, 27.1, 25.7, 22.5, 14.0.

(c) Synthesis of N-((4-(2-aminoethoxy)-3-methoxyphenyl)methyl)-9Z-octadecenamide:

N-((4-(2-azidoethoxy)-3-methoxyphenyl)-methyl)-9Z-octadecenamide (139 gm, 0.286 mole) is added to MeOH (1 L) in a 2 L flask. The mixture is warmed to dissolve all the substrate. Stannous chloride dihydrate (97 gm, 0.43 mole) is ground in a mortar and pestle and delivered all at once to the reaction solution. The flask is then fitted with a short Vigreux column and a bubbler to monitor gas evolution. The pale yellow-green solution warms and gives a steady evolution of gas for 20 minutes. The reaction is stirred a total of one hour. The content of the reaction vessel is poured into a 2 L graduated cylinder and fresh MeOH is added until the volume is 2 L. One-half of this solution is worked up at a time. 1 L of the reaction solution is placed in a 6 L separatory funnel and 1N NaOH (1 L) is added, immediately forming a thick cheese-like precipitate. Na$_2$SO$_4$ (50 gm) is added and the mixture is vigorously shaken for five minutes. To the suspension is added EtAc (2 L) and the solution shaken until two layers form. 1200 ml of the aqueous phase is removed, H$_2$O (500 ml) is added and the solution is reshaken. The aqueous layers are then combined and extracted with EtAc (1 L). All the organic layers are combined, dried (MgSO$_4$), filtered and concentrated to give 125 gm (95%) of white solid. Purification is accomplished on a Waters Prep 500 HPLC (2 columns) by first equilibrating and eluting with CHCl$_3$ until nonpolar impurities are removed (8 L CHCl$_3$), then by eluting with CHCl$_3$/MeOH/triethylamine (94:3:3; 4 L). The various fractions are analyzed by TLC using butanol/acetic acid/H$_2$O (4:1:1); ninhydrin is used to develop the product spots. Yield =93 gm (70%). $^1$H NMR (CDCl$_3$) (ppm): 6.7 (s, 3H), 6.1 (m, 1H), 5.3 (t, 2H), 4.3 (d, 2H), 3.9 (t, 2H), 3.8 (s, 3H), 3.0 (t, 2H), 2.3–1.9 (m, 4H), 1.7–1.5 (m, 2H), 1.4 (s, 2H), 1.2 (s, 22H), 0.8 (t, 3H). $^{13}$C NMR (CDCl$_3$) (ppm): 172.8, 149.6, 131.8, 129.7, 119.9, 113.8, 111.6, 71.6, 55.7, 43.1, 41.4, 36.6, 31.7, 29.1, 27.1, 25.6, 22.5, 14.0.

EXAMPLE III

Synthesis of N-((4-(2-aminoethoxy)-3-methoxyphenyl)-methyl)-9Z-octadecenamide by the Phthalimide Synthesis Method

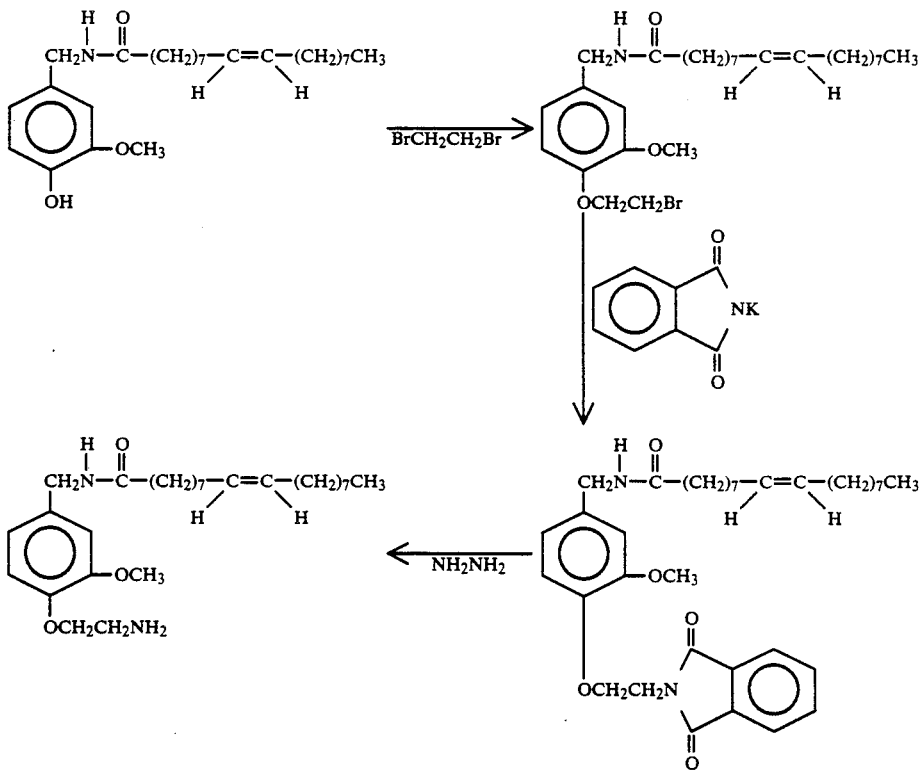

(a) Synthesis of N-((4-(2-bromoethoxy)-3-methoxyphenyl)-methyl)-9Z-octadecenamide is accomplished following the same procedure as described in Example II.

(b) Synthesis of N-((4-(2-phthalimidoethoxy)-3-methoxyphenyl)-methyl)-9Z-octadecenamide:

N-((4-(2-bromoethoxy)-3-methoxyphenyl)-methyl)-9Z-octadecenamide (615.5 gm, 1.17 moles) and DMF are combined in a 5 L flask equipped with a mechanical stirrer and a thermometer. The mixture is stirred and heated to 55° C. Once the solution becomes homogeneous, potassium phthalimide (270.0 gm, 1.47 mole) is added and the solution is maintained at 55° C. with good stirring. After ca. 10 minutes the reaction solution becomes homogeneous. Precipitation of a white solid then begins and the reaction is allowed to stir overnight at 55° C. TLC (acetone/dichloromethane 6:94) indicates when the starting material has been consumed. The reaction solution is divided into three equal volumes and each is worked up as follows: The solution is poured into a 4 L beaker and then diluted with water to the 3500 mL mark. After standing for ca. 15 minutes the solution is divided again into two equal parts, each of which is diluted to 3500 mL with water. The white precipitate is removed by filtration and washed several times with water. The three portions are combined and dried in a vacuum oven at 90° C. for 12 hours to give 682.25 g (98%) of a fine powder. Mp 109.5°–111.0° C. $^1$H NMR (CDCl$_3$)(ppm): 7.8 (m, 4H), 6.8 (m, 3H), 5.8 (m, 1H), 5.3 (t, 2H), 4.3 (d, 2H), 4.2 (t, 2H), 4.1 (t, 2H), 3.7 (s, 3H), 2.2–2.0 (m, 4H), 1.6 (m, 2H), 1.2 (s, 22H), 0.9

(t, 3H). $^{13}$C NMR (CDCl$_3$)(ppm): 172.8, 167.9, 150.0, 147.1, 133.9, 132.5, 132.1, 129.7, 123.1, 120.0, 114.9, 112.0, 66.2, 55.7, 43.2, 37.1, 36.7, 31.8, 29.3, 27.1, 25.7, 22.6, 14.0. IR (cm$^{-1}$): 3300, 1775, 1715, 1635, 1265, 1230, 1145, 1035, 1025, 720, CI-DEP Mass spectrum (m/z): 591 (MH+).

(c) Synthesis of N-((4-(2-aminoethoxy)-3-methoxyphenyl)-methyl)-9Z-octadecenamide:

N-((4-(2-phthalimidoethoxy)-3-methoxyphenyl-methyl)-9Z-octa-decenamide (250 gm, 0.424 mole) and ethanol (2500 mL) are combined in a 4 L beaker. The slurry is mechanically stirred and heated to 60° C. At ca. 45° C. the solution becomes homogeneous. 1-Hexene (20 mL) is added. Hydrazine hydrate (106 mL of a 64% aqueous solution) is then added. In ca. 5 minutes a white precipitate begins to form. During the 2 hour reaction time 500 mL of ethanol is added to the reaction to replenish that volume lost to evaporation. The reaction solution is then divided into three equal portions and each is worked up as follows: Methyl t-butyl ether (1.5 L) is used to transfer the slurry into a 4 L separatory funnel. Water (1 L) and 1N NaOH (500 mL) are added and the solution is thoroughly shaken. 50% NaOH (25 mL) is added and the solution is reshaken. The organic phase is then extracted twice with alkali using the same sequence, and washed with brine. The extract is dried over sodium sulfate and concentrated. The crude product is taken up in hot methyl t-butyl ether and allowed to crystallize. The crystals are filtered and dried in a vacuum desicator to give 124.87 g. A second crop of crystals, 40.82 g, is obtained to give 85% total yield. Mp 102°-106° C. $^1$H NMR (CDCl$_3$)(ppm): 6.7 (s, 3H), 6.1 (m, 1H), 5.3 (t, 2H), 4.3 (d, 2H), 3.9 (t, 3H), 3.8 (s, 3H), 3.0 (t, 2H), 2.5 (s, 2H), 2.1-1.6 (m, 4H), 1.5-1.2 (m, 2H), 1.2 (s, 22H), 0.9 (t, 3H). $^{13}$C NMR (CDCl$_3$)(ppm): 172.9, 149.3, 147.2, 131.8, 129.6, 119.7, 113.5, 111.4, 70.9, 55.5, 42.9, 40.9, 36.4, 31.6, 29.0, 26.9, 25.6, 22.4, 13.8. IR max (cm$^{-1}$): 3380, 3300, 1630, 1375, 1255, 1235, 1020, 800, 720 cm$-1$. CI-DEP Mass Spectrum (m/z): 461 (MH+).

EXAMPLE IV

Synthesis of
N-((4-(2-methyl-2-aminopropoxy)-3-methoxyphenyl)-methyl)-9Z-octadecenamide by the Aziridine Method To a solution of 2,2-dimethylaziridine (5.42 g; 0.076 mole; sold by Polysciences, Inc., Warrington, Pa.) in pyridine (100 mL) cooled in an ice bath, is added p-toluenesulfonyl chloride (21.81 g; 0.114 mole) in one portion. The reaction is stirred at 0° C. for 2 hours; diluted with ether (400 mL); washed with cold 10% H$_3$PO$_4$(2×150 mL), with a saturated NaHCO$_3$ solution (3×150 mL) and brine (1×150 mL); and dried over MgSO$_4$. Rotary evaporation of the solution affords a yellowish solid which is crystallized from ethyl acetate to yield the product 2,2-dimethylN-p-toluenesulfonyl-aziridine (4.48 g). $^1$H NMR (CDCl$_3$): 1.53 (6H, s), 2.45 (5H, m), 7.2-8.0 ppm (4H, m, aromatics).

A dispersion of KH (35% in oil; 68 mg; 0.595 mmole) is added to a dry round-bottom flask under argon and washed with n-pentane (3×5 mL) to remove the oil. The isolated KH is then suspended in dry DMF (5 mL) and treated in one portion with N-vanillyloleamide (248 mg; 0.595 mmole; which is prepared as described in U.S. Pat. No. 4,493,848, to LaHann and Buckwalter, issued Jan. 15, 1985, incorporated herein by reference in its entirety) and stirred for 1 hour at room temperature. The 2,2-dimethyl-N-p-toluenesulfonyl-aziridine (136 mg; 0.60 mmole) is then added and the resulting mixture is stirred at 50° C. for 16 hours. The DMF is rotary evaporated and the residue partitioned between water and ethyl acetate (50 mL). The organic layer is washed with water (4×20 mL), dried over MgSO$_4$ and rotary evaporated to yield a light brown oil (400 mg) which is purified by using silica gel chromatography (Chromatotron, 2 mm plate, eluting with 40% ethyl acetate/hexanes) to yield the p-toluenesulfonamido-blocked intermediate as a colorless oil, (140 mg; 40%). $^1$H NMR (CDCl$_3$): 0.93 (3H, t), 1.30 (29H, m), 2.05 (6H, m), 2.42 (3H, s), 3.65 (2H, s), 3.86 (3H, s), 4.38 (2H, d), 5.37 (2H, t), 5.7 (1H, s), 6.00 (1H, br s), 6.77 (3H, m, aromatics), 7.1-7.8 ppm (4H, m, tosyl aromatics).

A solution of the p-toluenesulfonamido-blocked intermediate (2.46 g; 3.8 mmoles) in dry THF (10 mL) is stirred at −60° C. under argon and treated with freshly condensed NH$_3$ until a final volume of 20 mL is achieved. This solution is then allowed to reflux gently under a dry ice condenser while small flakes of freshly cut sodium are slowly added. When a blue color persists for more than 5 minutes without the addition of more sodium, the reaction is quenched by the addition of solid ammonium acetate and evaporated under a gentle stream of nitrogen. The remaining solid is then partitioned between ether (500 mL) and NaOH solution (1N,

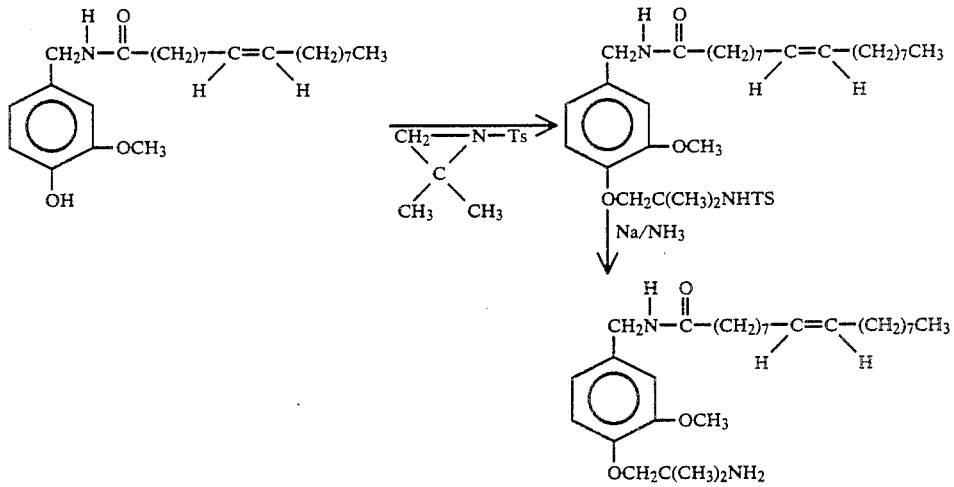

200 mL). The organic layer is washed with water (2×100 mL), dried over Na$_2$SO$_4$, and rotary evaporated to yield crude N-((4-(2-methyl-2-aminopropoxy)-3-methoxyphenyl)-methyl)-9Z-octadecenamide (1.75 g). This yellowish oil is purified using silica gel column chromatography eluting first with ethyl acetate to remove nonpolar impurities, then with methanol/methylene chloride (50%) to bring off the amine (1.1 g; 59%). $^1$H NMR (CDCl$_3$): 0.90 (3H, t), 1.23 (6H, s), 1.30 (22H, s), 1.87 (2H, s), 2.10 (6H, m), 3.73 (2H, s) 4.38 (2H, d), 5.38 (2H, t, alkene), 5.93 (1H, br s), 6.83 ppm (3H, s, aromatic). $^{13}$C NMR (CDCl$_3$): 13.77, 22.35, 25.51, 26.05, 26.88, 28.97, 31.53, 36.24, 42.74, 49.77, 55.67, 79.09, 111.86, 113.95, 19.73, 129.32, 129.56, 131.71, 147.91, 149.58, 172.76 ppm.

EXAMPLE V

Carrageenan Rat Paw Edema Test

Compounds of the present invention are tested for anti-inflammatory activity using the Carrageenan Rat Paw Edema Test.

Male Sprague Dawley rats (Charles River Breeding Laboratories Inc.) are weighed and food fasted overnight. The animals are divided into four to six groups of six animals each according to body weights, average about 145 g, so that each group has about the same average weight (within 10 g).

The following morning five ml of water is dosed orally via stomach tube to each animal to facilitate paw swelling. Thirty minutes later the animals are dosed with the test compound and then placed in individual cages. The compound of the present invention is dissolved in distilled deionized water with 1 equivalent of 1N acetic acid and delivered via stomach tube in 1 ml volume.

One hour after dosing the test compound, the animals are placed in a plastic restrainer and 50 ul of a 1% (w/w) carrageenan solution in 0.9% saline is injected into the ventral surface of the left rear paw. Paw volumes (0 time) are determined on both hind paws with a mercury displacement device equipped with a transducer and digitizer following the carrageenan injection. Four hours after the carrageenan injection, the paw volumes are again determined.

The results are expressed as percent inhibition of the mean paw volume of the test group relative to the control group according to the formula:

$$(C - T_{a..n})/C \times 100 = \text{Percent Inhibition}$$

where C is the average difference in paw volume before and after carrageenan-induced swelling, and $T_{a..n}$ is the difference in paw swelling in the treated animals (a..n). Statistical differences are determined by one way analysis of variance.

The compound N-((4-(2-aminoethoxy)-3-methoxyphenyl)methyl)-9Z-octadecenamide of the present invention has the following anti-inflammatory activity:

| Dose (mg/kg) | % Inhibition |
|---|---|
| 25 | 53.5 |
| 50 | 73.7 |
| 100 | 64.9 |
| 200 | 61.4 |

EXAMPLE VI

Rodent Hot Plate Test

The degree of thermal analgesia obtained is determined using the "rodent hot plate test" (RHP). The RHP system is designed to detect and evaluate agents which elevate the threshold for the perception of pain. Classically, this method has been utilized primarily to evaluate opioid (narcotic) analgesic agents, such as morphine. Unless administered in toxic quantities, antipyretic analgesics, such as aspirin or acetaminophen, exhibit little or no activity in the RHP system.

Male Sprague-Dawley rats (Charles River Breeding Laboratories Inc.) weighing between 100 and 125 grams upon arrival are used to evaluate the compounds of the present invention. Animals are double housed in stainless steel cages, and are fed Purina Rat Chow and tap water ad libitum. The animals are food fasted the afternoon proceeding the day of the study, and food is returned 5 hours post-treatment. Animals not being dosed by oral gavage are not fasted.

The apparatus for evaluating analgesic activity consists of an insulated copper hot plate whose surface is maintained at 55°±0.5° C. by a circulating water bath. A bottomless glass container (12" (30 cm) tall by 8" (20 cm) diameter) is used to restrict the animal to a defined area of the hot plate. After dosing, the animal is placed through the top opening of the container, and a stop watch is started when the animal makes contact with the plate. The stop-watch is stopped upon either of the following visually observed end points: (1) licking or biting of either hind paw, or (2) jumping. If the jump is not successful but both hind paws leave the surface of the plate in an effort to jump, this is considered jumping. The stop-watch is stopped at the end point and the animal is immediately removed from the hot plate. The time (latency) between the initial contact of the animal on the hot plate and the endpoint is recorded. A 60 second cut off is used during the assay so that if the end point is not exhibited within 60 seconds, the animal is removed from the hot plate and given a score of greater than 60 seconds.

Prior to dosing, animals are tested on the hot plate. This is denoted as pretest or base line latency. Usually, the animals are dosed by oral gavage, using a 1 cubic cm glass syringe connected to a size 8 french catheter. The dose volume is 5 ml/kg. On occasion, the animals are dosed by either subcutaneous administration or intravenous injection. Using the subcutaneous administration, a 1 ml tuberculin syringe is connected to a 25 gauge 5/8 inch needle, and injected under the skin in the neck or back region. For intravenous dosing, a 1 ml tuberculin syringe is connected to a 25 gauge ⅜ inch winged infusion set, and injected into the tail vein. The dose volume for subcutaneous and intravenous routes is 1 ml/kg. The latency times are typically recorded at 1.5, 3, 5, and 24 hours post-treatment. Much shorter times are recorded for an intravenous administration.

The mean latency times for orally dosed compounds of the present invention are provided in Tables I, II, and III. The mean latency times for orally dosed codeine phosphate are provided in Table IV. These latency times indicate that the compounds of the present invention are potent and efficacious analgesic agents, with N-((4-(2-aminoethoxy)-3-methoxyphenyl)-methyl)-9Zoctadecenamide being at least as potent and efficacious as the known opiate codeine.

TABLE I

N-((4-(2-aminoethoxy)-3-methoxyphenyl)-methyl)-9Z-octadecenamide

| Dose[1] | Mean Latency Times - Pretest and Hours Post Dose (sec.) | | | | |
|---|---|---|---|---|---|
| (mg/kg) | Pretest | 1.5 hr | 3 hr | 5 hr | 24 hr |
| 0 | 7.3 | 10.4 | 9.5 | 8.8 | 8.4 |
| 75 | 8.9 | 21.8 | 18.9 | 18.7 | 11.2 |
| 150 | 9.0 | 30.6 | 18.9 | 15.0 | 11.5 |
| 300 | 7.8 | 30.7 | 22.6 | 21.0 | 16.5 |

[1]Administered orally; 8 animals per dose group

TABLE II

N-(9Z-octadecenyl)-4-(2-aminoethoxy)-3-methoxyphenylacetamide

| Dose[1] | Mean Latency Times - Pretest and Hours Post Dose (sec.) | | | | |
|---|---|---|---|---|---|
| mg/kg | Pretest | 1.5 hr | 3 hr | 5 hr | 24 hr |
| 0 | 8.6 | 10.2 | 9.7 | 8.9 | 7.7 |
| 10 | 7.9 | 6.7 | 15.3 | 13.5 | 9.1 |
| 25 | 7.7 | 10.5 | 11.2 | 10.8 | 8.0 |
| 50 | 7.6 | 24.5 | 12.2 | 10.6 | 15.9 |
| 100 | 7.8 | 16.4 | 13.4 | 11.9 | 21.5 |

[1]Administered orally; 8 animals per dose group.

TABLE III

N-((4-(2-aminoethoxy)-3-methoxyphenyl)-methyl)-nonanamide

| Dose[1] | Mean Latency Times - Pretest and Hours Post Dose (sec.) | | | |
|---|---|---|---|---|
| mg/kg | Pretest | 3 hr | 5 hr | 24 hr |
| 0 | 6.1 | 6.4 | 6.5 | 6.8 |
| 50 | 6.3 | 7.5 | 7.2 | 8.1 |
| 100 | 5.9 | 9.9 | 10.2 | 12.3 |
| 200 | 6.8 | 10.8 | 16.4 | 22.0 |
| 300 | 6.1 | 14.1 | 14.6 | 20.3 |

[1]Administered orally; 8 animals per dose group.

TABLE IV

Codeine Phosphate

| Dose[1] | Mean Latency Times - Pretest and Hours Post Dose (sec.) | | | |
|---|---|---|---|---|
| (mg/kg) | Pretest | 1 hr | 2 hr | 4 hr |
| 0 | 7.3 | 6.9 | 6.6 | 6.2 |
| 50 | 7.0 | 8.7 | 6.4 | 6.5 |
| 100 | 7.4 | 8.5 | 8.9 | 6.0 |
| 200 | 6.9 | 16.9 | 21.0 | 11.7 |
| 400 | 6.7 | 26.5 | 28.4 | 24.6 |

[1]Administered orally; 8 animals per dose group.

EXAMPLE VII

Mouse Abdominal Constriction Assay

Compounds of the present invention are tested for analgesic activity using the mouse abdominal constriction assay. This assay is described in Hendershot and Forsaith, *J. Pharmacol. Exo. Therapeut.*, 125, pp. 237–240 (1959); and in *Methods in Narcotics Research*, Ehrenpreis and Neidle, Eds. (Marcel Dekker, Inc., New York; 1975), pp. 64–65; the disclosures of both these references being incorporated in their entirety herein by reference.

Male CF-1 mice (Charles River Breeding Laboratories, Inc.), weighing approximately 20 grams and food fasted overnight, are used in these assays. Test compounds are prepared for oral (p.o.) or subcutaneous (s.c.) administration, with compounds of the present invention being prepared in acidified (1N acetic acid) distilled deionized water so that the appropriate dose is given in 0.2 mls to a 20 gram mouse.

One and one half hours after administration of the test compound N-((4-(2-aminoethoxy)-3-methoxyphenyl)-methyl)-9Z-octadecenamide (p.o. or s.c.), an intraperitoneal (i.p.) injection of 0.02% phenylquinone (2.5 mg/kg) is given at a concentration of 0.25 ml/20 grams body weight. Ten minutes after the i.p. injection of phenylquinone, the number of full body writhes are counted for the succeeding ten minutes. Percent analgesia in this assay is calculated as follows:

$$\frac{\text{Control number of writhes} - \text{Dosed number of writhes}}{\text{Control number of writhes}} \times 100$$

The oral dose response and subcutaneous dose response for N-((4-(2-aminoethoxy)-3-methoxyphenyl)-methyl)-9Z-octadecenamide of the present invention are provided in Table V and Table VI respectively. The oral dose response and subcutaneous dose response for N-vanillyloleamide, which is disclosed in U.S. Pat. No. 4,493,848 to LaHann and Buckwalter, issued Jan. 15, 1985, are provided in Table VII and Table VIII respectively. The N-vanillyloleamide is tested for analgesic activity at 3 hours post-dose rather than at 1.5 hours post-dose since this is the time at which this compound demonstrates its peak analgesic effect.

The N-((4-(2-aminoethoxy)-3-methoxyphenyl)-methyl)-9Z-octadecenamide compound of the present invention is structurally the same as the N-vanillyloleamide except for the 2-aminoethoxy substitution on the phenyl ring. However, compared with the N-vanillyloleamide dosed orally, the compound of the present invention dosed orally demonstrates substantially greater analgesic potency at a substantially lower dose.

TABLE V

Oral Dose Response for N-((4-(2-aminoethoxy)-3-methoxyphenyl)-methyl)-9Z-octadecenamide

| Dose (mg/kg) | % Analgesia |
|---|---|
| 10 | 55.8 |
| 25 | 71.7 |
| 75 | 88.3 |
| 150 | 95.5 |
| 300 | 93.2 |

TABLE VI

Subcutaneous Dose Response for N-((4-(2-aminoethoxy)-3-methoxyphenyl)-methyl)-9Z-octadecenamide

| Dose (mg/kg) | % Analgesia |
|---|---|
| 1 | 22.3 |
| 2 | −13.7 |
| 4 | 34.3 |
| 8 | 57.8 |
| 10 | 91.4 |
| 100 | 99.0 |

TABLE VII

Oral Dose Response for N-Vanillyloleamide[1]

| Dose (mg/kg) | % Analgesia (3 hrs post-dose)[2] |
|---|---|
| 100 | 36 |
| 200 | 60 |
| 400 | 79 |

[1]Disclosed in U.S. Pat. No. 4,493,848, to LaHann and Buckwalter, issued January 15, 1985.
[2]At time of peak analgesic effect.

TABLE VIII

Subcutaneous Dose Response for N-Vanillyloleamide[1]

| Dose (mg/kg) | % Analgesia (3 hrs post-dose)[2] |
|---|---|
| 0.75 | 35.4 |
| 1.5 | 62.8 |
| 2.25 | 76.1 |

[1]Disclosed in U.S. Pat. No. 4,493,848, to LaHann and Buckwalter, issued January 15, 1985
[2]At time of peak analgesic effect.

Example VIII

A composition for oral administration is prepared by combining the following ingredients:

| | |
|---|---|
| N-((4-(2-aminoethoxy)-3-methoxyphenyl)-methyl)-9Z-octadecenamide | 1.10 kg |
| Sesame oil | 6.50 liters |

The octadecenamide is dissolved in the sesame oil with the aid of sonication and is packaged in soft gelatin capsules using methods known in the art. Two of the resulting capsules, each containing 225 mg of the composition, are administered to a 60 kg human in need of treatment, producing analogesia and reducing inflammation.

A substantially similar reduction of inflammation and an increased analgesic effect is obtained when the N-((4-(2-aminoethoxy)-3-methoxyphenyl)-methyl)-9Z-octadecenamide is replaced with N-((4-(2-aminoethyxy)-3-methoxyphenyl)-methyl)-nonanamide; N-((4-(2-methyl-2-aminopropoxy)-3-methoxyphenyl)-methyl)-9Z-octadecenamide; N-((4-(2(S)-amino-3-metylbutoxy)-3methoxyphenyl)-methyl)-9Z-octadecenamidel N-(9Z-octadecenyl)-4-(2-aminoethoxy)-3-methoxy-phenylacetamide; N-octanyl-4-(2-aminoethoxy)-3-methoxyphenylacetamide; N-((4-(2-amino-3-hydroxypropoxy)-3-methoxyphenyl)-methyl)-9Z-octadecenamide; N-((4-(2-amino-2-carboxyethoxy)-3-methoxyphenyl)-methyl)-9Z-octadecenamide; and the pharmaceutically-acceptable salts and amides thereof.

Capsules for oral administration are also prepared by combining the following ingredients:

| | |
|---|---|
| N-((4-(2-aminoethoxy)-3-methoxyphenyl)-methyl)-9Z-octadecenamide | 100 mg |
| Lactose | 50 mg |
| Microcrystalline cellulose | 50 mg |

EXAMPLE IX

A composition for oral administration is prepared by combining the following ingredients:

| | |
|---|---|
| N-(9Z-octadecenyl)-4-(2-aminoethoxy)-3-methoxy-phenylacetamide | 250 g |
| Propylene glycol | 1800 ml |
| Ethyl alcohol | 175 ml |
| Distilled water | 75 ml |
| Artificial Cherry flavor | 10 ml |
| FD&C Red #40 | 0.2 g |

The above ingredients are combined to produce a syrup and are packaged under sterile conditions in 6 oz. bottles. One teaspoon of this formulation is administered to a 70 kg adult human, reducing inflammation and producing analgesia.

A substantially similar reduction of inflammation and analgesic effect is obtained when the N-(9Z-octadecenyl)-4-(2-aminoethoxy)-3-methoxy-phenylacetamide is replaced with N-((4-(2-aminoethoxy)-3-methoxyphenyl)-methyl)-9Z-octadecenamide; N-((4-(2aminoethoxy)-3-methoxyphenyl)-methyl)-nonanamide; N-((4-(2-methyl-2-aminopropoxy)-3-methylbutoxy)-3-methoxyphenyl)methyl)-9Z-octadecenamide; N-octanyl-4-(2-aminoethoxy)-3-methoxyphenylacetamide; N-((4-(2-amino-3-hydroxypropoxy)-3-methoxyphenyl)-methyl)-9Z-octadecenamide; N-((4-(2-amino-2-carboxyethoxy)-3-methoxyphenyl)-methyl)-9Z-octadecenamide; N-((4-(2-(S)-amino-3methylbutoxy)-3-methoxyphenyl)methyl)-9Z-octadecenamide; and the pharmaceutically-acceptable salts and amides thereof.

EXAMPLE X

A composition for topical administration is prepared by combining the following ingredients:

| | |
|---|---|
| N-((4-(2-methyl-2-aminopropoxy)-3-methoxyphenyl)-methyl)-9Z-octadecenamide | 4 g |
| Propylene glycol | 100 ml |
| Ethyl alcohol | 100 ml |

The octadecenamide is dissolved in a solution containing the other ingredients. Application of 0.4 ml of the resulting liquid to a 80 cm² portion of the forearm of a 60 kg human produces local analgesia which lasts approximately two days. Little or no skin irritation is observed.

A substantially similar local analgesic effect is obtained when the N-((4-(2-methyl-2-aminopropoxy)-3-methoxyphenyl)-methyl)-9Z-octadecenamide is replaced with N-((4-(2-methyl-2-aminopropoxy)-3-methoxyphenyl)-methyl)-nonanamide; N-((4-(2-(S)-amino-3methylbutoxy)-3-methoxyphenyl)-methyl)-9Z-octadecenamide; N-(9Z-octadecenyl)-4-(2-aminoethoxy)-3-methoxyphenylacetamide; N-octanyl-4-(2-aminoethoxy)-3-methoxyphenylacetamide; N-((4-(2-amino-3-hydroxypropoxy)-3-methoxyphenyl)-methyl)-9Z-octadecenamide; N-((4-(2-amino-2-carboxyethoxy)-3-methoxyphenyl)-methyl)-9Z-octadecenamide; and the pharmaceutically-acceptable salts and amides thereof.

EXAMPLE XI

Tablets are prepared by conventional methods, such as mixing and direct compaction, formulated as follows:

| Ingredient | mg per tablet |
|---|---|
| N-((4-(2-aminoethoxy)-3-methoxyphenyl)-methyl)-nonanamide | 100 |
| Microcrystalline cellulose | 100 |
| Sodium Starch glycolate | 30 |
| Magnesium stearates | 5 |

One tablet is administered orally to a patient in need of analgesia two times daily to provide general analgesia.

Similar results are achieved with tablets formulated as above but replacing the N-((4-(2-aminoethoxy)-3-methoxyphenyl)-methyl)-nonanamide, with N-((4-(2-aminoethyl)-3-methoxyphenyl)methyl)-9Z-octadecenamide; N-((4-(2-methyl-2-aminopropoxy)-3methoxyphenyl)-methyl)-9Z-octadecenamide; N-((4-(2(S)-amino-3-methylbutoxy)-3-methoxyphenyl)-9Z-octadecenamide; N-(9Z-octadecenyl)-4-(2-aminoethoxy)-3-methoxyphenylacetamide; N-octanyl-4-(2-aminoethoxy)-3-methoxyphenylacetamide; N-((4-(2-amino-3-hydroxypropoxy)-3-methoxyphenyl)-methyl)-9Z-octadecenamide; N-((4-(2-amino-2-carboxyethoxy)-3-methoxyphenyl)-methyl)-9Z-octadecenamide; and the pharmaceutically-acceptable salts and amides thereof.

EXAMPLE XII

Injectable compositions are prepared as follows:

| Component | Weight % |
|---|---|
| Composition 1: | |
| N-((4-(2-aminoethoxy)-3-methoxyphenyl)-methyl)-9Z-octadecenamide | 0.05% |
| Aqueous Acetic Acid (1.30%) | 95.45% |
| Dextrose | 4.50% |
| Composition 2: | |
| N-((4-(2-aminoethoxy)-3-methoxyphenyl)-methyl)-9Z-octadecenamide | 0.05% |
| Aqueous Sodium Acetate (1.18%) | 85.95% |
| Aqueous Acetic Acid (2.0%) | 10.00% |
| Benzyl Alcohol | 4.00% |
| Composition 3: | |
| N-((4-(2-aminoethoxy)-3-methoxyphenyl)-methyl)-nonanamide | 0.05% |
| Propylene Glycol | 99.95% |
| Composition 4: | |
| N-(9Z-octadecenyl)-4-(2-aminoethoxy)-3-methoxyphenylacetamide | 0.05% |
| Polyethylene Glycol: Propylene Glycol (1:3) | 99.95% |

The injection of 0.05 ml of Composition 2 prior to oral surgery for a 3rd molar extraction provides local anesthesia during the surgery and long-lasting local analgesia following the surgery.

Similar local analgesia benefits are obtained by locally infiltrating the surgical site with Compositions 1, 3 or 4 immediately following a surgery to provide long-lasting analgesia for surgical site pain.

EXAMPLE XIII

N-(4-(2-nitrophenoxy)-3-methoxyphenylmethyl)-nonanamide

In a 50 mL flask is placed a 24% potassium hydride dispersion (4.11 grams). The flask is stoppered and flushed with argon. Dry tetrahydrofuran (5 mL) is syringed into the flask. The mixture is stirred briefly and then the potassium hydride is allowed to settle. The tetrahydrofuran is removed with a syringe. 4-Hydroxy-3-methoxy-phenylmethylnonanamide (3.00 grams) is dissolved in dry N,N-dimethylformamide (15 mL) and slowly syringed into the flask. Hexamethylphosphoramide (4.0 mL) is syringed into the flask. The mixture is stirred under argon for one hour. 1-Chloro-2-nitrobenzene (3.56 grams) dissolved in dry N,N-dimethylformamide (5 mL) is syringed into the flask. The mixture is heated at 52° C. for 18 hours. Rotary evaporation of the solvents affords a residue which is mixed with 10% aqueous citric acid (50 mL), ethyl acetate (500 mL) and benzene (100 mL). The organic layer is washed with water (13×200 mL), dried over sodium sulfate, and rotary evaporated to a volume of about 15 mL. This solution is chromatographed on silica gel (Kieselgel 60 silica gel, 230-400 mesh) eluting with a mixture of ethyl acetate/hexanes (20/80) followed with ethyl acetate/hexanes (75/25). Rotary evaporation of the compound-containing fractions yields 3.997 grams crude product which is crystallized from hot ethyl acetate and hexanes to give N-(4-(2-nitrophenoxy)-3-methoxyphenylmethyl)-nonanamide (2.86 g, 72%, mp 93°-93.5° C.).

N-(4-(2-aminophenoxy)-3-methoxyphenylmethyl)-nonanamide

N-(4-(2-nitrophenoxy)-3-methoxyphenylmethyl)-nonanamide (1.23 g) is dissolved in methanol (50 mL). To this is added 10% palladium on charcoal (100.1 mg). The mixture is placed on a Paar shaker for 60 minutes at room temperature and 42 psi hydrogen. The mixture is filtered through celite, evaporated to dryness on a rotary evaporator, then dried overnight at room temperature and reduced pressure (0.5 mm Hg) to yield N-(4-(2-aminophenoxy)-3-methoxyphenylmethyl)nonanamide (1.11 g, 97%).

What is claimed is:

1. Substituted phenyl compounds having the structure:

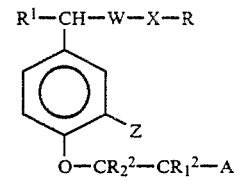

wherein:
(a) the —W—X— moiety is selected from the group consisting of —C(O)NH—, —C(S)NH—, —S(O)$_2$NH—, —NHC(O)O—, —NHC(S)O—, —NHC(O)NH— and —NHC(S)NH— wherein either available bond of the —W—X— moiety is bonded to the —R moiety and the remaining bond is attached to the benzyl carbon atom;
(b) —A is selected from the group consisting of halogen and phthalimide;
(c) —Z is selected from the group consisting of hydrogen, hydroxy, and methoxy;
(d) —R is an alkyl group having from about 1 to about 24 carbon atoms;
(e) —R$^1$ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and
(f) each —R$^2$ is independently selected from hydrogen, halogen, unsubstituted or substituted alkyl having from about 1 to about 6 carbon atoms, substituted or unsubstituted aryl, and carboxylate, or two —R$^2$ moieties are covalently bonded to form a substituted or unsubstituted alkyl, heteroalkyl, aryl or heteroaryl ring having from about 3 to about 8 atoms in the ring including from 0 to about 3 tereroatoms.

2. Substituted phenyl compounds having the structure:

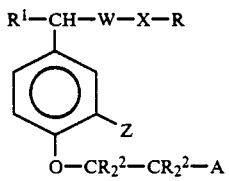

wherein:
(a) the —W—X— moiety is selected from the group consisting of —C(O)NH—, —C(S)NH—, —S(O)₂NH—, —NHC(O)O—, —NHC(S)O—, —NHC(O)NH— and —NHC(S)NH— wherein either available bond of the —W—X— moiety is bonded to the —R moiety and the remaining bond is attached to the benzyl carbon atom;
(b) —A is selected from the group consisting of halogen and —N₃;
(c) —Z is selected from the group consisting of hydrogen, hydroxy, and methoxy;
(d) —R is an alkyl group having from about 1 to about 24 carbon atoms;
(e) —R¹ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and
(f) each —R² is independently selected from hydrogen, halogen, unsubstituted or substituted alkyl having from about 1 to about 6 carbon atoms, substituted or unsubstituted aryl, and carboxylate, or two —R₂ moieties are covalently bonded to form a substituted or unsubstituted alkyl, heteroalkyl, aryl or heteroaryl ring having from about 3 to about 8 atoms in the ring including from 0 to about 3 heteroatoms.

3. Methods for synthesizing beta-aminoethoxy phenyl compounds, said methods comprising the steps of:
(a) reacting, to form a beta-haloethoxy phenyl compound:
(i) a phenol compound having the structure:

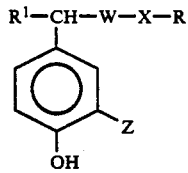

wherein: the —W—X— moiety is selected from the group consisting of —C(O)NH—, —C(S)NH—, —S(O)₂NH—, —NHC(O)O—, —NHC(S)O—, —NHC(O)NH— and —NHC(S)NH— wherein either available bond of the —W—X— moiety is bonded to the —R moiety and the remaining bond is attached to the benzyl carbon atom; —Z is selected from the group consisting of hydrogen, hydroxy, and methoxy; —R is an alkyl group having from about 1 to about 24 carbon atoms; —R¹ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and (ii) a vicinal dihalide having the structure:

X—CR₂²CR₂²—X wherein: X is halogen; and each —R² is independently selected from hydrogen, halogen, unsubstituted or substituted alkyl having from about 1 to about 6 carbon atoms, substituted or unsubstituted aryl, and carboxylate, or two —R₂ moieties are covalently bonded to form a substituted or unsubstituted alkyl, heteroalkyl, aryl or heteroaryl ring having from about 3 to about 8 atoms in the ring including from 0 to about 3 heteroatoms; followed by
(b) reacting the beta-haloethoxy phenyl compound with an azide salt to form a beta-azidoethoxy phenyl compound; followed by
(c) reducing the azido moiety to an amino moiety to form the beta-aminoethoxy phenyl compound.

4. Methods for synthesizing beta-aminoethoxy phenyl compounds, according to claim 3, said methods comprising the steps of:
(a) reacting the phenol compound with a vicinal dibromide having the structure Br—CR₂²CR₂²—Br to form a beta-bromoethoxy phenyl compound; followed by
(b) reacting the beta-bromoethoxy phenyl compound with an azide salt to form a beta-azidoethoxy phenyl compound; followed by
(c) reducing the azido moiety with SnCl₂ to an amino moiety to form the beta-aminoethoxy phenyl compound.

5. Methods for synthesizing beta-aminoethoxy phenyl compounds, said methods comprising the steps of:
(a) reacting, to form a nitrogen-substituted beta-aminoethoxy phenyl compound:
(i) a phenol compound having the structure:

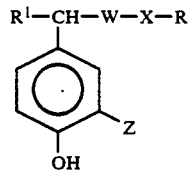

wherein: the —W—X— moiety is selected from the group consisting of —C(O)NH—, —C(S)NH—, —S(O)₂NH—, —NHC(O)O—, —NHC(S)O—, —NHC(O)NH— and —NHC(S)NH— wherein either available bond of the —W—X— moiety is bonded to the —R moiety and the remaining bond is attached to the benzyl carbon atom; —Z is selected from the group consisting of hydrogen, hydroxy, and methoxy; —R is an alkyl group having from about 1 to about 24 carbon atoms; and —R¹ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and
(ii) an aziridine compound having the structure:

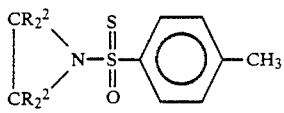

wherein each —R² is independently selected from hydrogen, halogen, unsubstituted or substituted alkyl having from about 1 to about 6 carbon atoms, substituted or unsubstituted aryl, and carboxylate, or two —R² moieties are covalently bonded to form a substituted or unsubstituted alkyl, heteroalkyl, aryl or heteroaryl ring having from about 3 to about 8 atoms in the ring including from 0 to about 3 heteroatoms; followed by (b) reducing the nitrogen substituent off of the nitrogen-substituted beta-aminoethoxy phenyl compound to form the beta-aminoethoxy phenyl compound.

6. Methods for synthesizing beta-aminoethoxy phenyl compounds, according to claim 5, said methods comprising the steps of:

(a) reacting the phenol compound as its phenolic anion with the aziridine compound; followed by (b) reducing the nitrogen substituent off of the nitrogen-substituted beta-aminoethoxy phenyl compound with sodium metal in liquid ammonia.

7. Methods for synthesizing beta-aminoethoxy phenyl compounds, said methods comprising the steps of:

(a) reacting, to form a beta-haloethoxy phenyl compound:
  (i) a phenol compound having the structure:

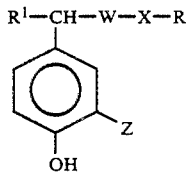

wherein: the —W—X— moiety is selected from the group consisting of —C(O)NH—, —C(S)NH—, —S(O)₂NH—, —NHC(O)O—, —NHC(S)O—, —NHC(O)NH— and —NHC(S)NH— wherein either available bond of the —W—X— moiety is bonded to the —R moiety and the remaining bond is attached to the benzyl carbon atom; —Z is selected from the group consisting of hydrogen, hydroxy, and methoxy; —R is an alkyl group having from about 1 to about 24 carbon atoms; —R¹ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and (ii) a vicinal dihalide having the structure:

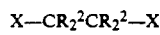

wherein: X is halogen; and each —R² is independently selected from hydrogen, halogen, unsubstituted or substituted alkyl having from about 1 to about 6 carbon atoms, substituted or unsubstituted aryl, and carboxylate, or two —R² moieties are covalently bonded to form a substituted or unsubstituted alkyl, heteroalkyl, aryl or heteroaryl ring having from about 3 to about 8 atoms in the ring including from 0 to about 3 heteroatoms; followed by (b) reacting the beta-haloethoxy phenyl compound with a phthalimide salt to form a beta-phthalimidoethoxy phenyl compound; followed by (c) reacting the beta-phthalimidoethoxy phenyl compound with hydrazine to remove the phthalimido group and form the beta-aminoethoxy phenyl compound.

8. Methods for synthesizing beta-aminoethoxy phenyl compounds, according to claim 7, said methods comprising the steps of:

(a) reacting the phenol compound with a vicinal dibromide having the structure Br—CR₂—CR₂—Br to form a beta-bromoethoxy phenyl compound; followed by (b) reacting the beta-bromoethoxy phenyl compound with a phthalimide salt to form a beta-phthalimido group and form the beta-aminoethoxy phenyl compound.

9. Methods for producing analgesia and reducing inflammation in humans or lower animals, said methods comprising administering to a human or lower animal in need of analgesia or reduced inflammation a safe and effective amount of a compound, and the pharmaceutically-acceptable salts and amides thereof, having the general structure:

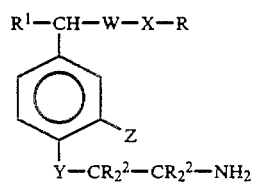

wherein:
(a) the —W—X— moiety is selected from the group consisting of —C(O)NH—, —C(S)NH—, —S(O)₂NH—, —NH(O)O—, —NH(S)O—, —NH(O)NH— and —NH(S)NH— wherein either available bond of the —W—X— moiety is bonded to the —R moiety and the remaining bond is attached to the benzyl carbon atom;

(b) —Y— is a moiety selected from the group consisting of —O—, —S— and —NR⁴—, where —R⁴ is selected from hydrogen and C₁-C₄ alkanyl;

(c) —Z is selected from the group consisting of hydrogen, hydroxy, and methoxy;

(d) —R is an alkyl group having from about 1 to about 24 carbon atoms;

(e) —R¹ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and (f) each —R² is independently selected from hydrogen, halogen, unsubstituted or substituted alkyl having from about 1 to about 6 carbon atoms, substituted or unsubstituted aryl, and carboxylate, or two —R² moieties are convalently bonded to form a substituted or unsubstituted alkyl or aryl ring having from about 3 to about 8 carbon atoms in the ring; wherein any alkyl ring substituent is selected from the group consisting of halogen, hydroxy, amino, aryl, carboxylate, and —OR$^3$ wherein —R$^3$ is unsubstituted alkyl having from about 1 to about 3 carbon atoms; and wherein ay aryl subsitutent is selected from the group consisting of halogen, hydroxy, C$_1$-C$_6$ alkoxy, amino, nitro, cyano, phenyl, benzyl, benzyloxy, trifluoromethylk, formylamino, carboxylate and C$_1$-C$_6$ alkyl.

10. Methods of claim 9 wherein —Y— is —O—; —R$^1$ is hydrogen; both —R$^2$ on the alpha carbon atom are hydrogen; both —R$^2$ on the beta carbon atom are selected from hydrogen and alkyl having from 1 to about 5 carbon atoms, or the —R$^2$ are covalently bonded to form an alkyl ring having from about 3 to about 6 carbon atoms, the alkyl or alkyl ring being unsubstituted or substituted with phenyl; and —Z is methoxy.

11. Methods for producing analgesia and reducing inflammation in humans or lower animals, said methods comprising administering to a human or lower animal in need of analgesia or reducing inflammation a safe and effective amount of a compound, and the pharmaceutically-acceptable salts and amides thereof, having the general structure:

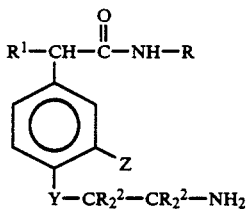

wherein:
 (a) =Q is selected from the group consisting of oxygen or sulfur;
 (b) —Y— is a moiety selected from the group consisting of —O—, —S— and —NR$^4$—, where —R$^4$ is selected from hydrogen and C$_1$-C$_6$ alkanyl;
 (c) —Z is selected from the group consisting of hydrogen, hydroxy, and methoxy;
 (d) —R is an alkyl group having from about 1 to about 24 carbon atoms;
 (e) —R$^1$ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and
 (f) each —R$^2$ is independently selected from hydrogen, halogen, unsubstituted or substituted alkyl having from about 1 to about 6 carbon atoms, substituted or unsubstituted aryl, and carboxylate, or two —R$^2$ moieties are covalently bonded to form a substituted or unsubstituted alkyl or aryl ring having from about 3 to about 8 carbon atoms in the ring; wherein any alkyl ring substituent is selected from the group consisting of halogen, hydroxy, amino, aryl, carboxylate, and —OR$^3$ wherein —R$^3$ is unsubstituted alkyl having from about 1 to about 3 carbon atoms; and wherein any aryl substituent is selected from the group consisting of halogen, hydroxy, C$_1$-C$_6$ alkoxy, amino, nitro, cyano, phenyl, benzyl, benzyloxy, trifluoromethyl, formylamino, carboxylate and C$_1$-C$_6$ alkyl.

12. Methods of claim 11 wherein —Y— is —O—; =Q is =O; —R$^1$ is hydrogen; both —R$^2$ on the alpha carbon atom are hydrogen; both —R$^2$ on the beta carbon atom are selected from hydrogen and alkyl having from 1 to about 5 carbon atoms, or the —R$^2$ are covalently bonded to form an alkyl having from about 3 to about 6 carbon atoms, the alkyl or alkyl ring being unsubstituted or substituted with phenyl; and —R is selected from the group consisting of alkanyl groups having from about 6 to about 14 carbon atoms, alkenyl groups having from about 14 to about 22 carbon atoms, and alkynyl groups having from about 14 to about 22 carbon atoms.

13. Methods of claim 12 wherein —Z is methoxy; and —R is selected from the group consisting of n-hexanyl, n-heptanyl, n-octanyl, n-nonanyl, n-decanyl, n-undecanyl, n-dodecanyl, n-tridecanyl, n-tetradecanyl, tetradecenyl, pentadecenyl, hexadecenyl, heptadecenyl, octadecenyl, nonadecenyl, eicosenyl, docosenyl, octadecandienyl, nonadecadienyl, eicosadienyl, octadecatrienyl, eicosatrienyl, eicosatetraenyl, octadecynyl, nonadecynyl, eicosynyl, and docosynyl.

14. Methods of claim 13, wherein the compound is selected from the group consisting of N-(9Z-octadecenyl)-4-(2-aminoethoxy)-3-methoxyphenylacetamide, N-octanyl-4-(2-aminoethoxy)-3-methoxyphenylacetamide, N-(9Z-octadecenyl)-4-(2-amino-2-methylpropoxy)-3-methoxyphenylacetamide, and N-octanyl-4-(2-amino-2-methylpropoxy)-3-methoxyphenylacetamide.

15. Methods of claim 12, wherein all —R$^2$ are hydrogen.

16. Methods for producing analgesia and reducing inflammation in humans and lower animals, said methods comprising administering to a human or lower animal in need of analgesia or reduced inflammation a safe and effective amount of a compound, and the pharmaceutically-acceptable salts and amides thereof, having the general structure:

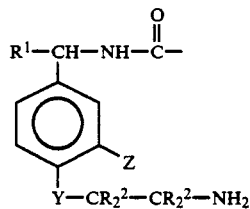

wherein:
 (a) =Q is selected from the group consisting of oxygen or sulfur;
 (b) —Y— is a moiety selected from the group consisting of —O—, —S— and —NR$^4$—, where —R$^4$ is selected from hydrogen and C$_1$-C$_6$ alkanyl;
 (c) —Z is selected from the group consisting of hydrogen, hydroxy, and methoxy;
 (d) —R is an alkyl group having from about 1 to about 24 carbon atoms;
 (e) —R$^1$ is selected from the group consisting of hydrogen, hydroxy, alkyl esters of hydroxy having from about 1 to about 5 carbon atoms, alkyl having from about 1 to about 5 carbon atoms, and alkoxy having from about 1 to about 5 carbon atoms; and
 (f) each —R$^2$ is independently selected from hydrogen, halogen, unsubstituted or substituted alkyl having from about 1 to about 6 carbon atoms, substituted or unsubstituted aryl, and carboxylate, or two —R$^2$ moieties are covalently bonded to form a substituted or unsubstituted alkyl or aryl ring having from about 3 to about 8 carbon atoms in the ring; wherein any alkyl ring substituent is selected from the group consisting of halogen, hydroxy, amino, aryl, carboxylate, and —OR$^3$ wherein —R$^3$ is unsubstituted alkyl having from about 1 to about 3 carbon atoms; and wherein any aryl substituent is selected from the group consisting of halogen, hydroxy, C$_1$-C$_6$ alkoxy, amino, nitro, cyano, phenyl, benzyl, benzyloxy, trifluoromethyl, formylamino, carboxylate and C$_1$-C$_6$ alkyl.

17. Method of claim 16, wherein —Y— is —O—; =Q is =O; —R$^1$ is hydrogen; both —R$^2$ on the alpha carbon atom are hydrogen; both —R$^2$ on the beta carbon atom are selected from hydrogen and alkyl having from 1 to about 5 carbon atoms, or the —R$^2$ are covalently bonded to form an alkyl ring having from about 3 to about 6 carbon atoms, the alkyl or alkyl ring being unsubstituted or substituted with phenyl; and —R is selected from the group consisting of alkanyl groups having from about 6 to about 14 carbon atoms, alkenyl groups having from about 14 to about 22 carbon atoms and alkynyl groups having from about 14 to about 22 carbon atoms.

18. Methods of claim 17, wherein —Z is methoxy; and —R is selected from the group consisting of n-hexanyl, n-heptanyl, n-octanyl, n-nonanyl, n-decanyl, n-undecanyl, n-dodecanyl, n-tridecanyl, tridecenyl, tetradecenyl, pentadecenyl, hexadecenyl, heptadecenyl, octadecenyl, nonadecenyl, eicosenyl, docosenyl, heptadecadienyl, octadecadienyl, nonadecadienyl, eicosadienyl, heptadecatrienyl, octadecatrienyl, nonadecatrienyl, eicosatrienyl, nonadecatetraenyl, heptadecynyl, octadecynyl, nonadecynyl, and eicosynyl.

19. Methods of claim 18, wherein the compound is selected from the group consisting of N-((4-(2-aminoethoxy)-3-methoxyphenyl)-methyl)-9Z-octadecenamide; N-((4-(2-aminoethoxy)-3-methoxyphenyl)-methyl)-nonanamide; N-((4-(2-methyl-2-aminopropoxy)-3-methoxyphenyl)-methyl)-9Z-octadecenamide; N-((4-(2(S)-amino-3-methylbutoxy)-3-methoxyphenyl)methyl)-9Z-octadecenamide; N-((4-(2-amino-3-hydroxypropoxy)-3-methoxyphenyl)-methyl)-9Z-octadecenamide; and N-((4-(2-amino-2-carboxyethoxy)-3-methoxyphenyl)-methyl)-9Z-octadecenamide.

20. Methods of claim 18, wherein both —R$^2$ on the beta carbon atom are selected from the group consisting of hydrogen, methyl, ethyl, and both —R$^2$ being covalently bonded to form a C$_3$-C$_5$ saturated alkyl ring; and —R is selected from the group consisting of n-heptanyl; n-octanyl, n-nonanyl, 8E— or 8Z-tridecenyl; 8E— or 8Z-pentadecenyl; 8E— or 8Z-heptadecenyl; 5E— or 5Z-heptadecenyl; 10E— or 10Z-heptadecenyl; 9E— or 9Z-octadecenyl; 12E— or 12Z-nonadecenyl; 8-methylene-1-heptadecanyl; 8Z, 11Z-heptadecadienyl; 8E, 11E-heptadecadienyl; 8Z, 11E-heptadecadienyl; 8Z, 10E-heptadecadienyl; 9E, 12E-octadecadienyl; 10E, 13E-nonadecadienyl; 8Z, 11Z, 14Z-heptadecatrienyl; 5Z, 8Z, 11Z-heptadecatrientyl; 10Z, 13Z, 16Z-nonadecatrienyl; 4Z, 7Z, 10Z, 13Z-nonadecatetraenyl; and 8-heptadecynyl.

21. Methods of claim 20, wherein the compound is selected from the group consisting of N-((4-(2-aminoethoxy)-3-methoxyphenyl)-methyl)-9Z-octadecenamide, N-((4-(2-aminoethoxy)-3-methoxyphenyl)-methyl)-nonanamide, N-((4-(2-methyl-2-aminopropoxy)-3-methoxyphenyl)-methyl)-9Z-octadecenamide, and N-((4-(2-methyl-2-aminopropoxy)-3-methoxyphenyl)-methyl)-nonanamide.

22. Methods of claim 20, wherein the compound is N-((4-(2-aminoethoxy)-3-methoxyphenyl)-methyl)-9Z-octadecenamide.

23. Methods of claim 17, wherein all —R$^2$ are hydrogen.

* * * * *

UNITED STATES PATENT AND TRADEMARK OFFICE
CERTIFICATE OF CORRECTION

PATENT NO. : 5,099,030  Page 1 of 3
DATED : March 24, 1992
INVENTOR(S) : J. H. Gardner, G. B. Kasting, T. L. Cupps, R. S. Echler and J. I. Shulman It is certified that error appears in the above-indentified patent and that said Letters Patent is hereby corrected as shown below:

Column 31, line 8, "$OCR_2{}^2\text{-}CR_2{}^2\text{-}Br$" should be --$OCR^2{}_2\text{-}CR^2{}_2\text{-}Br$--.

Column 31, line 24, "$OCR_2{}^2\text{-}CR_2{}^2\text{-}NH_2$" should be --$OCR^2{}_2\text{-}CR^2{}_2\text{-}NH_2$--.

Column 31, line 24, "$OCR_2{}^2\text{-}CR_2{}^2\text{-}N$" should be --$OCR^2{}_2\text{-}CR^2{}_2\text{-}N$--.

Column 31, line 54, "$O\text{-}CR_2{}^2\text{-}CR_2{}^2\text{-}A$" should be --$O\text{-}CR^2{}_2\text{-}CR^2{}_2\text{-}A$--.

Column 33, line 9, "$CR_2{}^2$" should be --$CR^2{}_2$--.

Column 33, line 12, "$CR_2{}^2$" should be --$CR^2{}_2$--.

Column 33, line 40, $OCR_2{}^2CR_2{}^2NH$" should be --$OCR^2{}_2CR^2{}_2NH$--.

Column 33, line 52, "$CR_2{}^2$" should be --$CR^2{}_2$--.

Column 33, line 59, $OCR_2{}^2CR_2{}^2NH$" should be --$OCR^2{}_2CR^2{}_2NH$--.

Column 48, line 32, "$O\text{-}CR_2{}^2CR_1{}^2\text{-}A$" should be --$O\text{-}CR^2{}_2CR^2{}_1\text{-}A$--.

Column 49, line 8, "$O\text{-}CR_2{}^2\text{-}CR_2{}^2\text{-}A$" should be --$O\text{-}CR^2{}_2\text{-}CR^2{}_2\text{-}A$--.

Column 51, line 1, "$CR_2{}^2$" should be --$CR^2{}_2$--.

Column 51, line 5, "$CR_2{}^2$" should be --$CR^2{}_2$--.

UNITED STATES PATENT AND TRADEMARK OFFICE
CERTIFICATE OF CORRECTION

PATENT NO. : 5,099,030  Page 2 of 3
DATED : March 24, 1992
INVENTOR(S) : J. H. Gardner, G. B. Kasting, T. L. Cupps, R. S. Echler and J. I. Shulman It is certified that error appears in the above-indentified patent and that said Letters Patent is hereby corrected as shown below:

Column 4, line 9, "$Y\text{-}CR_2{}^2\text{-}CR_2{}^2\text{-}NH_2$" should be --$Y\text{-}CR^2{}_2\text{-}CR^2{}_2\text{-}NH_2$--.

Column 5, line 34, "$Y\text{-}CR_2{}^2\text{-}CR_2{}^2\text{-}NH_2$" should be --$Y\text{-}CR^2{}_2\text{-}CR^2{}_2\text{-}NH_2$--.

Column 5, line 64, "$Y\text{-}CR_2{}^2\text{-}CR_2{}^2\text{-}NH_2$" should be --$Y\text{-}CR^2{}_2\text{-}CR^2{}_2\text{-}NH_2$--.

Column 6, line 9, "$Y\text{-}CR_2{}^2\text{-}CR_2{}^2\text{-}NH_2$" should be --$Y\text{-}CR^2{}_2\text{-}CR^2{}_2\text{-}NH_2$--.

Column 8, line 31, "$O\text{-}CR_2{}^2\text{-}CR_2{}^2\text{-}NH_2$" should be --$O\text{-}CR^2{}_2\text{-}CR^2{}_2\text{-}NH_2$--.

Column 15, line 68 to Column 16, line 2, "N-((4-(2-aminoe-thoxy)-3-methoxyphenyl)-methyl-N'-(9Z-octadecenyl )urea" should be --N-((4-2-amino-ethoxy)-3-methoxyphenyl)-methyl-N'-(9Z-octadecenyl)-urea--.

Column 28, line 42, "$OCR_2{}^2\text{--}CR_2{}^2\text{--}Br$" should be --$O\text{-}CR^2{}_2\text{-}CR^2{}_2\text{-}Br$--.

Column 28, line 44, "$Br\text{-}CR_2{}^2CR_2{}^2\text{-}Br$" should be --$Br\text{-}CR^2{}_2\text{-}CR^2{}_2\text{-}Br$--.

Column 28, line 53, "$OCR_2{}^2\text{-}CR_2{}^2\text{-}NH_2$" should be --$OCR^2{}_2\text{-}CR^2{}_2\text{-}NH_2$--.

Column 28, line 53, "$O\text{-}CR_2{}^2\text{-}CR_2{}^2\text{-}N_3$" should be --$O\text{-}CR^2{}_2\text{-}CR^2{}_2\text{-}N_3$--.

Column 29, line 16, "$O\text{-}CR_2{}^2\text{-}CR_2{}^2\text{-}A$" should be --$O\text{-}CR^2{}_2\text{-}CR^2{}_2\text{-}A$--.

Column 30, line 31, "$X\text{-}CR_2{}^2\text{-}CR_2{}^2\text{-}X$" should be --$X\text{-}CR^2{}_2\text{-}CR^2{}_2\text{-}X$--.

Column 31, line 6, "$Br\text{-}CR_2{}^2\text{-}CR_2{}^2\text{-}Br$" should be --$Br\text{-}CR^2{}_2\text{-}CR^2{}_2\text{-}Br$--.

UNITED STATES PATENT AND TRADEMARK OFFICE
CERTIFICATE OF CORRECTION

PATENT NO. : 5,099,030
DATED : March 24, 1992
INVENTOR(S) : J. H. Gardner, G. B. Kasting, T. L. Cupps, R. S. Echler and J. I. Shulman It is certified that error appears in the above-indentified patent and that said Letters Patent is hereby corrected as shown below:

Column 51, line 61, "$X-CR_2{}^2CR_2{}^2-X$" should be --$X-CR^2{}_2CR^2{}_2-X$--.

Column 52, line 37, "$Y-CR_2{}^2CR_2{}^2NH_2$" should be --$Y-CR^2{}_2CR^2{}_2NH_2$--.

Column 53, line 32, "$Y-CR_2{}^2CR_2{}^2NH_2$" should be --$Y-CR^2{}_2CR^2{}_2NH_2$--.

Column 54, line 45, "$Y-CR_2{}^2CR_2{}^2NH_2$" should be --$Y-CR^2{}_2CR^2{}_2NH_2$--.

Signed and Sealed this

Seventh Day of June, 1994

Attest:

BRUCE LEHMAN

*Attesting Officer*  *Commissioner of Patents and Trademarks*